(12) United States Patent
Dubewar et al.

(10) Patent No.: US 12,263,176 B2
(45) Date of Patent: Apr. 1, 2025

(54) PHARMACEUTICAL LIQUID COMPOSITIONS OF MELOXICAM

(71) Applicant: SLAYBACK PHARMA LLC, Princeton, NJ (US)

(72) Inventors: Ashish Anilrao Dubewar, Hyderabad (IN); Sumitra Ashokkumar Pillai, Hyderabad (IN); Pradeep Kumar Kare, Hyderabad (IN); Kumar Swamy Ummiti, Hyderabad (IN); Shanker Mamidi, Nalgonda (IN); Raghavender Rao Kategher, Vikarabad (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 25 days.

(21) Appl. No.: 18/542,163

(22) Filed: Dec. 15, 2023

(65) Prior Publication Data

US 2024/0139204 A1 May 2, 2024

Related U.S. Application Data

(63) Continuation of application No. 17/725,772, filed on Apr. 21, 2022, now abandoned, which is a continuation-in-part of application No. 17/368,367, filed on Jul. 6, 2021, now abandoned.

(30) Foreign Application Priority Data

Jul. 6, 2020 (IN) ............................. 202041028641

(51) Int. Cl.
A61K 31/5415 (2006.01)
A61K 47/10 (2017.01)
A61K 47/30 (2006.01)
A61K 47/38 (2006.01)
A61K 47/40 (2006.01)
A61K 47/44 (2017.01)

(52) U.S. Cl.
CPC .......... *A61K 31/5415* (2013.01); *A61K 47/10* (2013.01); *A61K 47/30* (2013.01); *A61K 47/38* (2013.01); *A61K 47/40* (2013.01); *A61K 47/44* (2013.01)

(58) Field of Classification Search
None
See application file for complete search history.

(56) References Cited

U.S. PATENT DOCUMENTS

| | | |
|---|---|---|
| 6,284,269 B1 | 9/2001 | Struengmann et al. |
| 6,551,619 B1 | 4/2003 | Penkler et al. |
| 7,459,283 B2 | 12/2008 | Wertz et al. |
| 8,512,727 B2 | 8/2013 | Cooper et al. |
| 8,920,820 B2 | 12/2014 | Folger et al. |
| 9,345,665 B2 | 5/2016 | Ryde et al. |
| 9,561,229 B2 | 2/2017 | Ottoboni et al. |
| 9,974,742 B2 | 5/2018 | Ottoboni et al. |
| 9,974,746 B2 | 5/2018 | Ryde et al. |
| 9,993,557 B2 | 6/2018 | Henke et al. |
| 10,098,891 B2 | 10/2018 | Folger et al. |
| 2002/0035107 A1 | 3/2002 | Henke et al. |
| 2003/0191187 A1 | 10/2003 | Lee et al. |
| 2005/0288280 A1 | 12/2005 | Friton et al. |
| 2009/0181080 A1 | 7/2009 | Kottayil et al. |
| 2010/0297252 A1 | 11/2010 | Cooper et al. |
| 2012/0213855 A1 | 8/2012 | Agarwal et al. |
| 2014/0303245 A1 | 10/2014 | Sprogoe et al. |
| 2016/0082013 A1 | 3/2016 | Ottoboni et al. |
| 2016/0206622 A1 | 7/2016 | Ottoboni et al. |
| 2017/0216205 A1 | 8/2017 | Ottoboni et al. |
| 2018/0133199 A1 | 5/2018 | Dellamary |
| 2019/0224332 A1 | 7/2019 | Patil et al. |
| 2020/0360268 A1 | 11/2020 | Sun et al. |
| 2021/0093642 A1 | 4/2021 | Muthaiyyan et al. |
| 2021/0106591 A1 | 4/2021 | Wang et al. |

FOREIGN PATENT DOCUMENTS

| | | | |
|---|---|---|---|
| KR | 2014-39663 A | | 4/2014 |
| WO | WO2008/062274 A2 | | 5/2008 |

(Continued)

OTHER PUBLICATIONS

Final Office Action issued by the U.S. Patent and Trademark office on Nov. 20, 2020, for patent appl cation No. U.S. Appl. No. 16/371,293.

(Continued)

*Primary Examiner* — Katherine Peebles

(74) *Attorney, Agent, or Firm* — Birch, Stewart, Kolasch & Birch, LLP

(57) ABSTRACT

The present invention relates to stable injectable compositions comprising meloxicam or its pharmaceutically acceptable salts, solvates, or hydrates thereof, wherein the composition is provided in a sealed container, e.g., an ampoule, vial and pre-filled syringe. Further, the present invention relates to a stable injectable solution comprising meloxicam or its pharmaceutically acceptable salts, solvates, or hydrates thereof, suitable for subcutaneous, intravenous or intramuscular administration. The invention relates to methods for manufacturing stable injectable solutions of meloxicam. The present invention further relates to a method of treating pain by parenterally administering to a patient in need thereof a composition comprising a stable solution of meloxicam, wherein said solution provides rapid onset of action for pain relief compared to a reference composition.

14 Claims, 1 Drawing Sheet

(56) References Cited

FOREIGN PATENT DOCUMENTS

WO     WO2011/086194 A1     7/2011
WO     WO2019/037757 A1     2/2019

OTHER PUBLICATIONS

International Search Report dated Jun. 25, 2019, for International Patent Application No. PCT/US2019/025293.
Machine English translation for KR10-2014-0039663 (Year 2014).
Non-Final Office Action issued by the U.S. Patent and Trademark office on Febraury 20, 2020, for U.S. Appl. No. 16/371,293.
Non-Final Office Action issued by the U.S. Patent and Trademark office on Oct. 11, 2019, for U.S. Appl. No. 16/371,293.
Siddharth, V et al., "Formulation and Characterization of Meloxicam Loaded Microemulsion for the Treatment of Rheumatoid Arthritis," World Journal of Pharmaceutical Research, 2014, vol. 3, Issue 3, pp. 4305-4335.
Written Opinion dated Jun. 25, 2019, for International Patent Application No. PCT/US2019/025293.
Yener, G., et al., "Effect of Vehicles on Release of Meloxicam from Various Topical Formulations," The Open Drug Delivery Journal, 2009, vol. 3, pp. 19-23.
Internet webpage obtained from Wikipedia website: https://en.wikipedia.org/wiki/Lecithin, Retrieved from Internet Nov. 18, 2020.

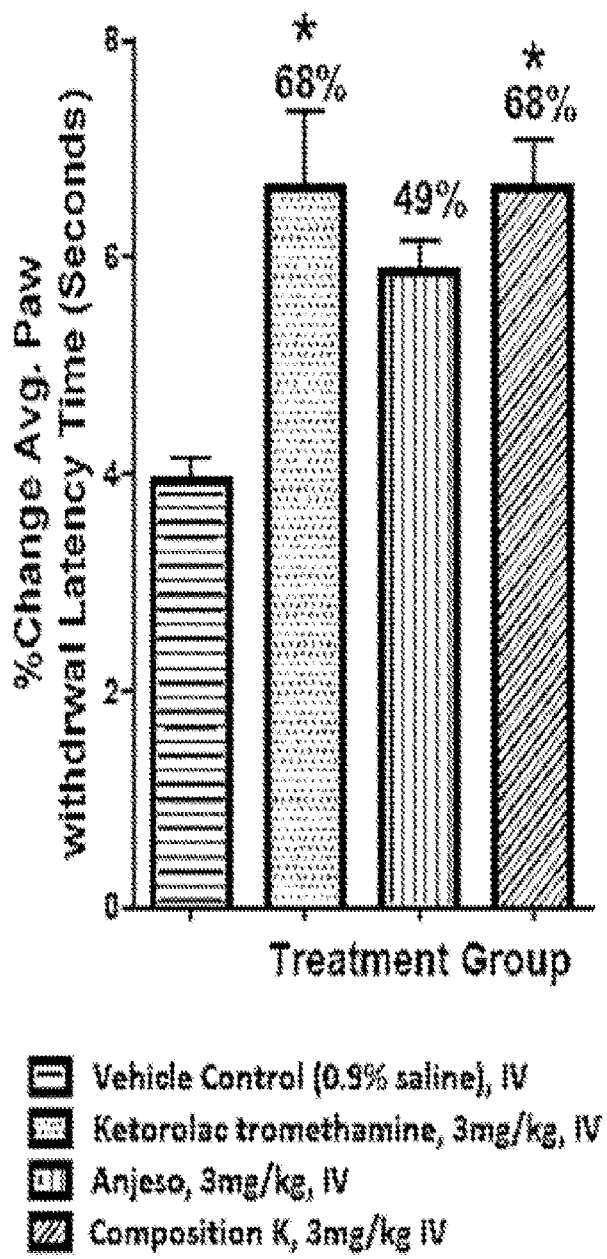

PHARMACEUTICAL LIQUID COMPOSITIONS OF MELOXICAM

CROSS-REFERENCE TO RELATED APPLICATIONS

This application is a Continuation of co-pending U.S. application Ser. No. 17/725,772 filed on Apr. 21, 2022, which is a continuation-in-part of U.S. application Ser. No. 17/368,367 filed on Jul. 6, 2021, which claims priority to foreign Application No. IN, 202041028641 filed on Jul. 6, 2020, which is incorporated herein by reference in its entirety.

FIELD OF THE INVENTION

The present invention relates to stable injectable compositions comprising meloxicam or its pharmaceutically acceptable salts, solvates, or hydrates thereof, wherein the composition is provided in a sealed container, e.g., an ampoule, vial and pre-filled syringe. Further, the present invention relates to a stable injectable solution comprising meloxicam or its pharmaceutically acceptable salts, solvates, or hydrates thereof, suitable for subcutaneous, intravenous or intramuscular administration. The invention further relates to methods for manufacturing stable injectable solutions of meloxicam.

BACKGROUND OF THE INVENTION

Meloxicam, an oxicam derivative, is a member of the enolic acid group of nonsteroidal anti-inflammatory drugs (NSAIDs). It is reported to be a selective inhibitor of cyclo-oxygenase-2 (COX-2) and exerts potent anti-inflammatory, anti-rheumatism and anti-pyretic activity. The chemical name of meloxicam is 4-hydroxy-2-methyl-N-(5-methyl-2-thiazolyl)-2H-1,2-benzothiazine-3-carbox-amide-1,1-dioxide and its chemical structure is represented by the structural Formula (I).

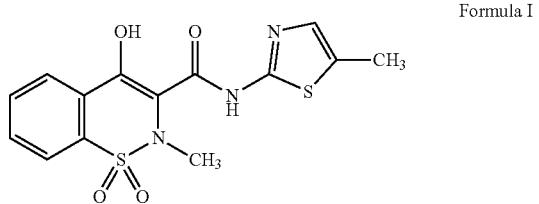 [SMILES: Cc1cnc(NC(=O)C2=C(O)c3ccccc3S(=O)(=O)N2C)s1]

Formula I

Meloxicam is practically insoluble in water, with higher solubility observed in strong acids and bases. It is very slightly soluble in methanol. Meloxicam has been approved for relieving signs and symptoms of osteoarthritis, relieving the signs and symptoms of rheumatoid arthritis, and treatment of lower back pain. Meloxicam is especially effective for treatment of all types of pain associated with inflammation.

Non-steroidal anti-inflammatory drugs (NSAIDs) like meloxicam, are useful in pain management because NSAIDs provide an analgesic effect without the sedation and addictive properties of narcotic analgesics. Furthermore, the long half-life of meloxicam makes it useful for long-lasting relief which is not provided by narcotic or opioid analgesics. However, due to their typically long onset of action, conventional NSAIDs, including meloxicam, are frequently inappropriate for management of acute pain.

The form of meloxicam earlier approved and marketed in the United States is MOBIC®, provided as 7.5 and 15 mg tablets. Mobic® is approved for relieving the signs and symptoms of osteoarthritis and rheumatoid arthritis. Meloxicam when administered orally has a slow onset of analgesic action, largely due to poor water solubility. It is therefore absorbed with a time delay after administration. It has a prolonged absorption, with the time of maximum observed plasma concentration ($T_{max}$) approximately 5-6 hours following oral administration, which is consistent with its poor aqueous solubility. Although meloxicam has an analgesic effect without sedation and addictive properties of narcotic analgesics, due to prolonged absorption in gastrointestinal tract and delayed onset of action and longer $T_{max}$, meloxicam is hampered to treat acute pain i.e., management of moderate-to-severe post-operative pain by oral administration.

Injectable formulations containing meloxicam are very challenging to manufacture as meloxicam is an insoluble drug displaying poor solubility characteristics. One means of addressing this challenge is to prepare an injectable dispersion which does not require complete solubilization of meloxicam.

Recently, an injectable formulation of meloxicam was approved by United States Food and Drug Administration (USFDA) under the brand name ANJESO® for the management of moderate-to-severe pain, alone or in combination with non-NSAID analgesics in adults. ANJESO® is formulated as an aqueous dispersion containing 30 mg/mL of meloxicam per vial. Anjeso® is an injectable formulation of meloxicam for the intravenous (IV) route of administration that uses a proprietary Nano Crystal® Colloidal Dispersion (NCD) technology. ANJESO® was approved by the USFDA under New Drug Application (NDA) Number 210583 and National Drug Code (NDC) Number 71518-001. Each mL of aqueous dispersion of ANJESO® contains 30 mg of meloxicam, 9 mg povidone, 3 mg sodium deoxycholate, 60 mg sucrose, and water for injection (herein after called as reference composition).

The recommended dose of ANJESO® is 30 mg once daily, administered as intravenous bolus injection over 15 seconds. However, ANJESCO® provides meaningful pain relief within a median time of only 2-3 hr after administration; it may not be useful in cases where a rapid onset of pain relief is required. Thus, it is desirable to have a non-NSAID analgesic with a rapid onset of effect for providing immediate relief of pain.

The in vivo performance of meloxicam when formulated as a dispersion for intravenous administration will be sensitive to variations in particle size distribution, particle agglomeration, particle charge (zeta potential), crystalline state, particle morphology, dose uniformity and rate of dissolution of particles in blood plasma. Injectable dispersions are also fundamentally unstable and it is difficult to ensure that the physical stability of the formulation is retained over the entire period of the shelf-life. These factors influence the quality & efficacy of finished product, which makes injectable dispersions being less preferred by physicians. Another drawback of injectable dispersion of meloxicam is the time it takes to provide a meaningful pain relief, which is 2 to 3 hours after administration.

The size reduction techniques to obtain smaller particles of meloxicam utilize complicated processes which are often cost intensive. Size reduction of the meloxicam require many steps like multiple crushing, milling and pulverizing.

In general, the size reduction machinery is massive, expensive and energy intensive and such units suffer unavoidable wear and tear that incurs substantial operational and maintenance costs. Use of such massive machinery and other specific requirements of the process for making such particles, further add up to the cost of manufacturing the drug formulation.

Because of the problems associated with the currently approved products of meloxicam, it is always desirable to develop an injectable meloxicam solution for human use, which is safe, therapeutically effective and easy to administer.

There exists a need for development of novel compositions of meloxicam that are ready-to-use or ready-to-dilute, and which minimizes or prevents degradation of meloxicam. There exists a need for developing stable, therapeutically effective, ready-to-use or ready-to-dilute injectable solutions of meloxicam suitable for human use.

It is further desirable to develop injectable meloxicam solution for human use which displays rapid onset of action and provides faster relief of pain, compared to the currently approved and marketed dosage forms of meloxicam.

It would also be desirable for inventive meloxicam solutions to remain stable over relevant period of time under suitable storage conditions and to be suitable for administration by intravenous or other parenteral routes.

Preparing a stable injectable solution of meloxicam is quite challenging due to the inherent poor solubility characteristics exhibited by meloxicam. Attempts have been made earlier in order to formulate stable injectable solution of meloxicam. However, until now, none of them have been successful in developing a stable injectable solution of meloxicam, particularly because of the poor solubility exhibited by meloxicam in aqueous solvents.

The present invention fulfils this need by developing novel injectable solutions of meloxicam and providing methods of efficient and safer use to achieve an improved standard of patient care.

SUMMARY OF THE INVENTION

In one aspect, the present invention relates to novel injectable solution of meloxicam, suitable for human use, for the prevention, treatment or management of acute or chronic pain.

In another aspect, the present invention relates to pharmaceutical compositions of meloxicam, suitable for human use, displaying rapid onset of action and providing faster relief of pain.

An aspect of the present invention relates to injectable solution of meloxicam and methods for preparing the compositions.

An aspect of the present invention relates to injectable solution of meloxicam, suitable for human use, for the prevention, treatment or management of moderate-to-severe pain.

In certain aspects, the inventive pharmaceutical compositions are suitable for subcutaneous, intravenous or intramuscular administration.

An aspect of the present invention relates to injectable solution of meloxicam suitable for intravenous administration.

In certain aspects, the inventive pharmaceutical compositions of meloxicam are suitable for intravenous bolus administration or intravenous infusion administration.

The inventive pharmaceutical compositions according to the invention may be provided in the form of aqueous or non-aqueous solution.

In another aspect of the present invention relates to pharmaceutical compositions of meloxicam for human use, suitable for intravenous administration, displaying rapid onset of action and providing faster relief of pain, compared to the currently approved and marketed dosage forms of meloxicam.

In another aspect, the inventive pharmaceutical compositions are provided in a sealed container selected from ampoules, vials and pre-filled syringes, preferably a sealed pre-filled syringe.

The inventive compositions are advantageously ready-to-use (RTU) or ready-to-dilute (RTD). An aspect of the invention relates to stable ready-to-use or ready-to-dilute meloxicam compositions suitable for intravenous administration.

Another aspect relates to stable ready-to-use or ready-to-dilute, liquid compositions of meloxicam, comprising one or more solvents and optionally one or more pharmaceutically acceptable excipients.

Yet another aspect of the present invention relates to solutions of meloxicam are suitable for intravenous administration, displaying rapid onset of action and providing faster relief of pain, compared to the currently approved and marketed dosage forms of meloxicam.

In an aspect, solutions suitable for intravenous administration comprises (a) therapeutically effective amount of meloxicam; (b) pharmaceutically acceptable solvent; and (c) one or more pharmaceutically acceptable excipients.

In an aspect, stable solutions suitable for intravenous administration comprises (a) therapeutically effective amount of meloxicam; (b) pharmaceutically acceptable solvent; and (c) one or more pharmaceutically acceptable excipients.

In an aspect, stable injectable solutions suitable for intravenous administration comprises (a) therapeutically effective amount of meloxicam; (b) pharmaceutically acceptable solvent; and (c) optionally, one or more pharmaceutically acceptable excipients.

In another aspect, stable injectable solutions suitable for intravenous administration comprises (a) therapeutically effective amount of meloxicam; (b) pharmaceutically acceptable solvent; and (c) optionally, one or more pharmaceutically acceptable excipients, wherein meloxicam is present at a concentration of about 5 mg/mL or more.

In another aspect, stable injectable solutions suitable for intravenous administration comprises (a) therapeutically effective amount of meloxicam; (b) pharmaceutically acceptable solvent; and (c) optionally, one or more pharmaceutically acceptable excipients, wherein meloxicam is present at a concentration of about 15 mg/mL or more.

In another aspect, stable injectable solutions suitable for intravenous administration comprises (a) therapeutically effective amount of meloxicam; (b) pharmaceutically acceptable solvent; and (c) optionally, one or more pharmaceutically acceptable excipients, wherein meloxicam is present at a concentration of about 30 mg/mL or more.

In an aspect, stable injectable solutions of meloxicam suitable for intravenous administration comprises (a) therapeutically effective amount of meloxicam; (b) pharmaceutically acceptable solvent; and (c) optionally, one or more pharmaceutically acceptable excipients selected from the group consisting of solubilizer, buffering agent, nucleation inhibiting agent, tonicity contributing agent, pH adjusting agent, antioxidant, chelating agent and preservative.

In an aspect, stable solutions of meloxicam suitable for intravenous administration comprises (a) therapeutically effective amount of meloxicam; (b) pharmaceutically acceptable solvent; and (c) one or more pharmaceutically acceptable excipients selected from the group consisting of solubilizer, buffering agent, nucleation inhibiting agent, tonicity contributing agent, pH adjusting agent, antioxidant, chelating agent and preservative.

In an aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients.

In an aspect, stable solutions of meloxicam suitable for parenteral administration comprises (a) therapeutically effective amount of meloxicam; (b) pharmaceutically acceptable solvent; (c) one or more solubilizers; and (d) one or more nucleation inhibitors e) optionally, one or more other pharmaceutically acceptable excipients.

In an aspect, stable solutions of meloxicam suitable for intravenous administration comprises (a) therapeutically effective amount of meloxicam; (b) one or more solvent (c) one or more solubilizer; and (d) one or more nucleation inhibitor e) optionally, one or more other pharmaceutically acceptable excipients.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein concentration of the solubilizer ranges from about 2.5 mg/mL to about 400 mg/mL.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the solution has a pH in the range of about 5 to about 12.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the solution is stable for at least 6 months at 40° C./75% RH.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the solution is stable for at least 6 months at 25° C./60% RH.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the solution is stable for at least 12 months at 25° C./60% RH.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the solution is stable for at least 12 months at 2-8° C.

In certain aspects, the composition according to the invention is stable for at least 3 months at 25° C. and 60% relative humidity. In certain embodiments, the composition according to the invention is stable for at least 3 months at 40° C. and 75% relative humidity. In certain embodiments, the composition according to the invention is stable for at least 24 months when stored under room temperature.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein the level of each impurity in the solution is less than about 2% w/w, preferably less than about 1.5% w/w, more preferably less than about 1% w/w, more preferably less than about 0.5% w/w as measured by HPLC.

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein in said stable solutions of meloxicam was bioequivalent to a commercially available meloxicam drug product Anjeso® (New Drug Application (NDA) Number 210583 and National Drug Code (NDC) Number 71518-001).

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein in said stable solutions of meloxicam was bioequivalent to a commercially available 30 mg/mL meloxicam drug product Anjeso® (New Drug Application (NDA) Number 210583 and National Drug Code (NDC) Number 71518-001).

In another aspect, stable solutions of meloxicam suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein in said composition upon intravenous administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125% or a combination thereof.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein concentration of the solubilizer ranges from about 2.5 mg/mL to about 400 mg/mL.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein the solution has a pH in the range of about 5 to about 10.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein the solution is stable for at least 6 months at 40° C./75% RH.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein the solution is stable for at least 12 months at 25° C./60% RH.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein the level of each impurity in the solution is less than about 2% w/w, preferably less than about 1.5% w/w, more preferably less than about 1% w/w, more preferably less than about 0.5% w/w, more preferably less than about 0.2% w/w as measured by HPLC.

In an aspect, stable solutions of meloxicam suitable for intravenous administration comprises (a) therapeutically effective amount of meloxicam; (b) one or more solvents (c) one or more solubilizers; and (d) one or more nucleation inhibitors e) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125% or a combination thereof.

Another aspect of the invention provides stable solutions of meloxicam suitable for intravenous administration comprising (a) therapeutically effective amount of meloxicam; (b) pharmaceutically acceptable solvent; (c) one or more solubilizers selected from arginine, lysine, meglumine, cyclodextrin derivative, diethanolamine, tromethamine or mixtures thereof; and (d) optionally, one or more other pharmaceutically acceptable excipients, wherein concentration of the solubilizer ranges from about 2.5 mg/mL to about 400 mg/mL.

Another aspect of the invention provides stable solutions of meloxicam suitable for intravenous administration comprising (a) therapeutically effective amount of meloxicam; (b) polyethylene glycol (c) meglumine, and (d) polyvinyl pyrrolidone e) optionally, one or more other pharmaceutically acceptable excipients, wherein the solution has a pH in the range of about 7 to about 10.

In certain aspects, the invention relates to methods for making a composition, which comprise: (i) dispensing 60% v/v water for injection; (ii) adding one or more solubilizing agents to form a first solution; (iii) adding meloxicam to the first solution to form a second solution; and (iv) optionally, adjusting the pH of the second solution by adding a suitable acid or base, e.g., hydrochloric acid and/or sodium hydroxide (v) final volume was made with 40% v/v water for injection.

In certain aspects, the invention relates to methods for making a composition, which comprise: (i) dispensing 60% v/v water for injection; (ii) adding one or more solubilizing agents to form a first solution; (iii) adding meloxicam to the first solution to form a second solution; (iv) adding nucleation inhibitor (v) adding one or more solvents/co-solvents (vi) optionally, adjusting the pH of the second solution by adding a suitable acid or base, e.g., hydrochloric acid and/or sodium hydroxide and (vii) final volume was made with 40% v/v water for injection.

An aspect of the present invention relates to a method of treating pain by parenterally administering to a patient in need thereof a composition comprising a stable solution of meloxicam, wherein said solution provides rapid onset of action for pain relief compared to a reference composition.

An aspect of the present invention relates to the method as described above wherein said composition comprises meloxicam in a solubilized form.

An aspect of the present invention relates to the method as described above wherein said composition comprises meloxicam; one or more solubilizers; a nucleation inhibitor; one or more pharmaceutically acceptable solvents; and optionally one or more other pharmaceutically acceptable excipients.

An aspect of the present invention relates to the method as described above wherein the meloxicam dose is 30 mg.

An aspect of the present invention relates to the method as described above, wherein the solubilizer is selected from a group comprising meglumine, cyclodextrin, cyclodextrin derivative, monoethanolamine, diethanolamine, tromethamine, hydroxypropyl methyl cellulose (HPMC), L-arginine, L-lysine, polysorbate 80 (Tween® 80), polysorbate 20 (Tween® 20), poloxamer, propylene glycol, glycerin, ethanol, polyethylene glycol (300 and 400), sorbitol, dimethylacetamide, and polyethoxylated castor oil (Cremophor® EL) or combinations thereof.

An aspect of the present invention relates to the method as described above, wherein the nucleation inhibitor is povidone.

An aspect of the present invention relates to the method as described above, wherein the administration of said composition provides the patient a rapid onset of pain relief without the use of a second NSAID.

An aspect of the present invention relates to the method as described above, wherein said meloxicam solution stored for 1 month at 40° C./75% RH has an amount of 2-Amino-5-methylthiazole that is less than about 0.2% w/w of meloxicam of the total composition.

An aspect of the present invention relates to the method as described above, wherein said composition stored for 6 months at 40° C./75% RH has an amount of 2-Amino-5-methylthiazolethat is less than about 0.2% w/w of meloxicam of the total composition.

An aspect of the present invention relates to the method as described above, wherein said composition stored for 1 month at 40° C./75% RH has an amount of 2-Amino-5-methylthiazole that is less than about 0.2% w/w of meloxicam of the total composition.

BRIEF DESCRIPTION OF DRAWINGS

FIG. 1 is comparison of % change in average pain withdrawal latency in rats administered with test compounds (i.e., Vehicle control (0.9% saline), ketorolac tromethamine (3 mg/kg; IV), Anjeso® (3 mg/kg; IV), Composition K (3 mg/kg; IV).

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail.

As used herein, "a," "an," "the," "at least one," and "one or more" are used interchangeably. As used herein, the term "or" is generally employed in its usual sense including "and/or" unless the content clearly dictates otherwise.

As used herein the term "meloxicam" refers to meloxicam free base or a pharmaceutically acceptable salt, solvate or hydrate thereof. It also includes geometric isomer or a stereoisomer thereof. In certain aspects, meloxicam free base may be used. Any crystalline form as well as the amorphous form of meloxicam may be used for the preparation of pharmaceutical compositions of the present invention.

The terms "about" and "approximate", when used along with a numerical variable, generally means the value of the variable and all the values of the variable within an experimental error (e.g., 95% confidence interval for the mean) or within a specified value±10% or within a broader range.

Within the context of the present invention, the term "ready-to-use" or "RTU" as used herein refers to an injectable composition that is stable and is not reconstituted from a lyophilizate. The term "ready-to-use" or "RTU" also encompasses within its scope, injectable compositions that are stable and does not require any reconstitution or dilution with parenterally acceptable diluent and can be directly administered to the patient.

Within the context of the present invention, the term "ready-to-dilute" or "RTD" as used herein refers to an injectable composition that is stable and is diluted with a suitable diluent for parenteral administration.

The terms "composition", "pharmaceutical composition", "pharmaceutical product", "dosage form", "pharmaceutical dosage form", "formulation", "pharmaceutical formulation", etc., refer to a pharmaceutical composition that may be administered to a patient in need of treatment, which may be in any conventional formulation. For example, the term "pharmaceutical composition" as used herein refers to a solution.

Within the context of this invention, the term "solution" refers to a mixture of one or more substances dispersed molecularly (i.e., dissolved) in a dissolving liquid medium or vehicle. The solution is preferably homogeneous, in the sense that the active pharmaceutical ingredient (API) is essentially uniformly distributed and concentrated in the solution. The liquid solution may be viscous or not. A solution differs from a suspension which comprises solid particles dispersed throughout a liquid phase in which they are not soluble. As used herein, the term "solution" further means a solution which does not contain any visible particulate matter, solid particle, liposome or nanoparticles. The solution provides % transmittance, when measured 650 nm, not less than 97 examples, not less than 98%, less than 99%, not less than 99.5%, not less than 99.6%, not less than 99.7% or not less than 99.8%.

The term "parenterally acceptable liquid vehicle", "vehicle", "solvent" and "parenterally acceptable liquid solvent" are interchangeable.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or colour. The term "stable" indicates both chemical and physical stability. The term "stable" can further mean as no more than about a 5% loss of meloxicam under typical commercial storage conditions. Preferably, formulations of the present inventions will have no more than about a 3% loss of meloxicam, more preferably, no more than about a 2% loss of melphalan, under typical commercial storage conditions.

The term "degradation product," as used herein, refers to an unwanted chemical or impurity (including, but not limited to known or unknown related substances) that can develop during the manufacturing, transportation, and storage of drug products and can affect the efficacy of pharmaceutical products. It can form in response to changes in light, temperature, pH, and humidity, or due to inherent characteristics of active ingredient, such as their reaction with excipients or on contact with the packaging.

The term "parenteral" or "injectable" refers to routes selected from subcutaneous (SC), intravenous (IV), intramuscular (IM), intradermal (ID), intraperitoneal (IP) and the like.

The expression "bioequivalent" or "bioequivalence" is a term of art and is intended to be defined in accordance with Approved Drug Products with Therapeutic Equivalence Evaluations, $41^{th}$ Edition, which is published by the U.S. Department of Health and Human Services, and is commonly known as the "Orange Book". Generally, bioequivalence can be defined as the absence of significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations whose rate and extent of absorption differ by −20%/+25% or less are generally considered to be bioequivalent.

The term "bolus dose" refers to a discrete amount of a medication or a drug, e.g., meloxicam, which is given within a specific time. The specific time over which the bolus dose is administered (also referred to herein as the infusion rate) may be any suitable time which provides rapid onset of action (i.e., pain relief) and which does not cause significant injection site pain, such as a significant burning sensation. In some embodiments, the infusion time may be about 1 minute or less.

The term "in vivo" in general means in the living body of a plant or animal, whereas the term "in vitro" generally means outside the body and in an artificial environment.

The term "subject" refers to an animal, including a human or non-human. The terms patient and subject may be used interchangeably herein. Non-human may be a rat, a dog, a mice or a guinea pig.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0\text{-}infinity}$" means the area under a plasma drug concentration—time curve from time point of 0 to infinity after drug administration.

The term "$AUC_{0\text{-}t}$" means the area under a plasma drug concentration—time curve from time point of 0 to t after drug administration, wherein t is time in hours and is in between 1 hour to 72 hours.

The term "shelf life" means the period beginning from manufacture of a formulation beyond which the formulation cannot be expected beyond reasonable doubt to yield the therapeutic outcome approved by a government regulatory agency.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

By "therapeutically effective" amount is meant the amount of a drug sufficient to treat, prevent, or ameliorate a condition in a subject or patient. The effective amount of meloxicam, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The objective of the present invention is to increase the solubility of meloxicam enabling formulation of meloxicam solution dosage form. Another objective of the present invention is to provide stable aqueous solutions of meloxicam having long-term storage stability.

The inventive pharmaceutical compositions described herein may be provided in the form of a solution suitable for injection. To prepare such composition, active drug is dissolved in a parenterally acceptable liquid vehicle. In certain non-limiting embodiments, meloxicam composition is formulated as a liquid and provided in the form of a solution. The pharmaceutically acceptable liquid vehicle or solvent may comprise water, water for injection, saline, dextrose solution, alcohol, ethanol, glycerine, polyol (for example, propylene glycol, and polyethylene glycol, and the like), dimethylacetamide, N-methylpyrollidone, dimethyl sulfoxide, ringer's solution, isotonic sodium chloride solution, or suitable mixtures thereof.

The inventive pharmaceutical compositions of the present invention may contain suitable pharmaceutically acceptable solvents or vehicle, but not limited to ethanol, propylene glycol, butanediol, isopropanol, tetrahydrofurfurol (THF), tetrahydrofuran polyethylene glycol ether, glycerol, dimethylacetamide, polyethylene glycol (e.g. polyethylene glycol 300, polyethylene glycol 400, polyethylene glycol 600), etc. preferably selected from the group consisting of ethanol, propylene glycol, butanediol, tetrahydrofurfurol, glycerol, polyethylene glycol 300, polyethylene glycol 400 and polyethylene glycol 600 and combination thereof.

In an embodiment of the invention, pharmaceutical compositions may contain one or more co-solvents, such as benzyl benzoate, polyethylene glycol (PEG), polypropylene glycol (PPG), propylene glycol (PG), N-methyl-pyrrolidone, dimethyl sulfoxide (DMSO), benzyl alcohol, methanol, ethanol, propanol, glycofurol, sorbitan monolaurate, tetrahydrofuran or dioxane, acetone or mixtures thereof.

In an embodiment of the invention, the ready-to-use or ready-to-dilute compositions may be formulated as aqueous or non-aqueous solutions. Preferably, the ready-to-use or ready-to-dilute compositions will include a vehicle in an amount from about 1 mL to greater than or equal to 100 mL.

According to the present invention, the ready-to-dilute compositions may be provided in a kit form along with parenterally acceptable diluent. Parenterally acceptable diluents include water for injection, 0.9% saline (normal saline), 0.45% saline (half normal saline) and 2.5% dextrose/0.45% saline.

In certain non-limiting embodiments, meloxicam is formulated as a composition, wherein meloxicam is the only therapeutically active ingredient present in the composition. In another non-limiting embodiment, meloxicam is formulated as a composition, wherein meloxicam is formulated in combination with at least one or more other therapeutically active ingredient.

The present application relates to injectable solution of meloxicam, particularly wherein meloxicam is present at a concentration of 5 mg/mL or more. In another aspect, a stable ready-to-use pharmaceutical compositions of the present application comprises meloxicam, wherein meloxicam is present at concentration about 5 mg/mL to about 60 mg/mL, preferably about 30 mg/mL.

Preferably, the stable ready-to-use pharmaceutical compositions for human use will be provided as a solution dosage form that is suitable for intravenous administration. The pharmaceutical compositions may be formulated according to conventional pharmaceutical practice. The compositions of the invention can be administered in any conventional manner. It will be readily appreciated by those skilled in the art how to administer compositions of the present invention to a human.

In certain aspects, the present application increases solubility of meloxicam by one or more of methods selected from (a) particle size reduction (b) solid dispersion (c) complexation (d) high-speed stirring and e) in situ salt formation.

Salt formation is a popular approach employed to increase the solubility of poorly soluble drug substances such as meloxicam. Processing a weak acid or base with a counterion can cause in situ salt formation, depending on the properties of the materials. Typically, counterions are small inorganic molecules (e.g., sodium, potassium, ammonium, hydrochloride, or phosphate ions) or small organic molecules (e.g., citrate, tartrate, succinate, mesylate or meglumine) which works by creating a favourable microenvironment to enhance solubility of the drug. The water solubility of a counterion can have a direct relationship to an increase in salt solubility.

In an embodiment, stable injectable ready-to-use solutions of meloxicam suitable for intravenous administration comprises (a) therapeutically effective amount of meloxicam; (b) pharmaceutically acceptable solvent; and (c) optionally, one or more pharmaceutically acceptable excipients.

In an embodiment, stable injectable ready-to-use solutions of meloxicam suitable for intravenous administration comprises (a) therapeutically effective amount of meloxicam; (b) pharmaceutically acceptable solvent; and (c) one or more pharmaceutically acceptable excipients.

In some embodiments, inventive pharmaceutical composition of the invention can be formulated for long-term storage of meloxicam at room temperature in presence of a suitable pharmaceutically-acceptable excipient. The pharmaceutically acceptable excipients can increase the half-life of meloxicam when stored at any temperature, such as room temperature. The presence of the pharmaceutical excipients can decrease the rate of decomposition of meloxicam at any temperature, such as room temperature.

The inventive pharmaceutical compositions of the present invention comprise one or more pharmaceutically acceptable liquid excipient(s) selected from, but are not limited to, solvents/co-solvents, surfactants, solubilizers, wetting agents, water immiscible solvents, water, water miscible solvents, hydrophilic solvents, hydrophobic solvents, preservatives, chelating agents, antioxidants, tonicity contributing agents, anti-foaming agents, buffering agents, pH adjusting agents, osmotic agents and the like or mixtures thereof.

In an embodiment, solubilizer increases the solubility of meloxicam in pharmaceutical acceptable vehicle. In a pharmaceutical composition, one or more solubilizers may be included. As used herein, the solubilizer may be selected from the group consisting of meglumine, cyclodextrin, cyclodextrin derivative, monoethanolamine, diethanolamine, tromethamine, hydroxypropyl methyl cellulose (HPMC), L-arginine, L-lysine, polysorbate 80 (Tween® 80), polysorbate 20 (Tween® 20), poloxamer, propylene glycol, glycerin, ethanol, polyethylene glycol (300 and 400), sorbitol, dimethylacetamide, and polyethoxylated castor oil (Cremophor® EL) and combinations thereof. In another embodiment, the pharmaceutical compositions of the present invention comprise meloxicam and a solubilizer, wherein the composition further comprises additional pharmaceutically acceptable excipients.

As stated above, meloxicam is insoluble in nature. The solubilizer meglumine has a rather favourable action to increase the solubility of meloxicam. A stable solution of meloxicam can be formulated using a solubilizing amount of meglumine. Meglumine is a carbohydrate derived from sorbitol in which the hydroxyl group in position one is replaced by a methylamine group. The increased applicability of meglumine relates to its ability to form adducts with carboxylic acids and markedly increases their solubility in aqueous solutions due to the presence of a large number of hydroxyl groups. Because of low toxicity and other favourable properties, it is suitable even for parenteral applications. A solution composition according to the present invention comprises meloxicam and a solubilizing amount of meglumine. In practice, it is advantageous to prepare a solution of meglumine in water and add meloxicam into such solution.

Because the solubilization of meglumine is different from that of ordinary pH adjuster, high-concentration meloxicam solution for human use, especially for parenteral administration, can be prepared when its pH value is adjusted back at 6 to 9 with pharmaceutically acceptable pH adjusters after it exceeds 9 during the course of preparation of meloxicam solution.

Cyclodextrin or its derivatives also has a favourable action to increase the solubility of meloxicam. In one embodiment, the cyclodextrin of the present invention includes α-cyclodextrin, β-cyclodextrin, δ-cyclodextrin, γ-cyclodextrin, or combinations thereof. In an embodiment, the cyclodextrin of the present application preferably includes either a substituted or non-substituted β-cyclodextrin.

Substituted cyclodextrins increase the solubility of the cyclodextrin and mitigate toxic effects associated with unsubstituted cyclodextrins. Examples of substituted β-cyclodextrins include those substituted with one or more hydrophilic groups, such as monosaccharide (e.g., glucosyl, maltosyl), carboxyalkyl (e.g., carboxylmethyl, carboxyethyl), hydroxyalkyl-substituted (e.g., hydroxyethyl, 2-hydroxypropyl) and sulfoalkylether-substituted-β-cyclodextrin.

In one embodiment, the cyclodextrin is a substituted β-cyclodextrin, particularly, hydroxypropyl-β-cyclodextrin (HP-β-CD) and sulfobutylether-β-cyclodextrin (SBE-β-CD). However, it is understood that typically any substitution to the cyclodextrin, including substitution by hydrophobic groups such as hydroxyalkyl substituted-cyclodextrin, will improve its aqueous solubility by disrupting the hydrogen bonding network within the crystal lattice of the solid cyclodextrin, thereby lowering the lattice energy of the solid. The degree of substitution is not believed to be critical; however, the degree of substitution is advantageously at least 1% and typically 2% to 10%, such as 3% to 6%.

In a preferred embodiment, the cyclodextrin derivative is a substituted β-cyclodextrin, particularly suitable β-cyclodextrins include for example but not limited to, Cavasol® W7 HP (hydroxypropyl-β-cyclodextrin (HP-β-CD), Kleptose® HP (hydroxypropyl-β-cyclodextrin (HP-β-CD)), Cavamax® W7 (β-cyclodextrin), Captisol® (sulfoalkylether-β-cyclodextrin), Cavasol® W7 M (methyl-β-cyclodextrin), Cavasol® W8 HP (hydroxypropyl-γ-cyclodextrin), Cavamax® W8 (γ-cyclodextrin), Cavamax® W6 (α-cyclodextrin). In one aspect, the cyclodextrin is 2-hydroxypropyl-β-cyclodextrin (HP-β-CD), which is a cyclic oligosaccharide containing seven D-(+)-glucopyranose units.

In an embodiment, stable injectable ready-to-use solution suitable for intravenous administration comprises (a) meloxicam; (b) water for injection; (c) meglumine; and (d) optionally, one or more additional pharmaceutically acceptable excipients.

In an embodiment, stable injectable meloxicam solution suitable for intravenous administration comprises (a) meloxicam; (b) water for injection; (c) meglumine; and (d) optionally, one or more additional pharmaceutically acceptable excipients.

In an embodiment, stable injectable meloxicam solution suitable for intravenous administration comprises (a) meloxicam; (b) water for injection; (c) L-arginine; and (d) optionally, one or more additional pharmaceutically acceptable excipients.

In an embodiment, stable injectable meloxicam solution suitable for intravenous administration comprises (a)

meloxicam; (b) water for injection; (c) EDTA; and (d) optionally, one or more additional pharmaceutically acceptable excipients.

In an embodiment, stable injectable meloxicam solution suitable for intravenous administration comprises (a) meloxicam; (b) water for injection; (c) buffer and e) optionally, one or more additional pharmaceutically acceptable excipients.

In an embodiment, stable injectable meloxicam solution suitable for intravenous administration comprises (a) meloxicam; (b) water for injection; (c) Sodium dihydrogen phosphate; (d) disodium hydrogen phosphate, and e) optionally, one or more additional pharmaceutically acceptable excipients.

In an embodiment, stable injectable meloxicam solution suitable for intravenous administration comprises (a) meloxicam; (b) water for injection; (c) TRIS and d) optionally, one or more additional pharmaceutically acceptable excipients.

In an embodiment, stable injectable meloxicam solution suitable for intravenous administration comprises (a) meloxicam; (b) water for injection; (c) pH adjusting agent and d) optionally, one or more additional pharmaceutically acceptable excipients.

In an embodiment, stable injectable meloxicam solution suitable for intravenous administration comprises (a) meloxicam; (b) water for injection; (c) hydrochloric acid and d) optionally, one or more additional pharmaceutically acceptable excipients.

In an embodiment, stable injectable meloxicam solution suitable for intravenous administration comprises (a) meloxicam; (b) water for injection; (c) sodium hydroxide and d) optionally, one or more additional pharmaceutically acceptable excipients.

In an embodiment, stable injectable meloxicam solution suitable for intravenous administration comprises (a) meloxicam; (b) water for injection; (c) meglumine; d) EDTA, e) optionally, one or more additional pharmaceutically acceptable excipients.

In an embodiment, stable injectable meloxicam solution suitable for intravenous administration comprises (a) meloxicam; (b) water for injection; (c) L-Arginine; d) HP-$\beta$-CD, e) optionally, one or more additional pharmaceutically acceptable excipients.

In an embodiment, stable injectable meloxicam solution suitable for intravenous administration comprises (a) meloxicam; (b) water for injection; (c) sodium dihydrogen phosphate monohydrate; d) disodium hydrogen phosphate anhydrous; e) polyethylene glycol; and f) optionally, one or more additional pharmaceutically acceptable excipients.

In an embodiment, stable injectable ready-to-use solution suitable for intravenous administration comprises (a) meloxicam; (b) water for injection; (c) hydroxypropyl-$\beta$-cyclodextrin (HP-$\beta$-CD) and (d) optionally, one or more additional pharmaceutically acceptable excipients.

In an embodiment, stable injectable ready-to-use solution suitable for intravenous administration comprises (a) meloxicam; (b) water for injection; (c) meglumine; (d) diethanolamine and (e) optionally, one or more additional pharmaceutically acceptable excipients.

In an embodiment, stable injectable ready-to-use solution suitable for intravenous administration comprises (a) meloxicam; (b) water for injection; (c) meglumine; (d) polyethylene glycol and (e) optionally, one or more additional pharmaceutically acceptable excipients.

In an embodiment, stable injectable ready-to-use solution suitable for intravenous administration comprises (a) meloxicam; (b) water for injection; (c) meglumine; (d) polyethylene glycol; (e) povidone and (f) optionally, one or more additional pharmaceutically acceptable excipients.

In an embodiment, stable injectable ready-to-use solution for intravenous administration comprises (a) meloxicam; (b) water for injection; (c) meglumine; (d) hydroxypropyl-$\beta$-cyclodextrin (HP-$\beta$-CD) and (e) optionally, one or more additional pharmaceutically acceptable excipients.

In an embodiment, stable injectable ready-to-use solution for intravenous administration comprises (a) meloxicam; (b) water for injection; (c) meglumine; (d) hydroxypropyl-$\beta$-cyclodextrin (HP-$\beta$-CD); (e) povidone and (f) optionally, one or more additional pharmaceutically acceptable excipients.

In an embodiment, inventive pharmaceutical composition according to the invention comprises meloxicam, meglumine and one or more additional solubilizer, wherein the concentration of solubilizer is from about 2.5 mg/mL to about 200 mg/mL.

In an embodiment, inventive pharmaceutical composition according to the invention comprises meloxicam and meglumine may for example be used in a molar ratio of 0.5:1 to 0.5:10.

In an embodiment, inventive pharmaceutical composition according to the invention comprises meloxicam and meglumine may for example be used in a molar ratio of 1:0.5 to 10:1.

In an embodiment, inventive pharmaceutical composition according to the invention comprises meglumine, wherein the meglumine concentration may be between 10 mg/mL and 50 mg/mL, preferably 15-30 mg/mL, more preferably 20 mg/mL.

In an embodiment, inventive pharmaceutical composition according to the invention comprises meloxicam and HP-$\beta$-CD may for example be used in a molar ratio of 0.5:1 to 0.5:10.

In an embodiment, inventive pharmaceutical composition according to the invention comprises meloxicam and polyethylene glycol may for example be used in a molar ratio of 0.5:1 to 0.5:10.

In an embodiment, inventive pharmaceutical composition according to the invention comprises meloxicam and polyethylene glycol may for example be used in a molar ratio of 1:0.1 to 10:1.

In an embodiment, inventive pharmaceutical composition according to the invention comprises meloxicam and povidone may for example be used in a molar ratio of 0.5:1 to 0.5:10.

In an embodiment, inventive pharmaceutical composition according to the invention comprises meloxicam and povidone may for example be used in a molar ratio of 1:0.1 to 10:1.

In another embodiment, inventive pharmaceutical composition according to the invention comprises meloxicam, meglumine and a cyclodextrin derivative, wherein the concentration of cyclodextrin is from about 5 mg/mL to about 200 mg/mL.

The inventive pharmaceutical compositions of the present invention may additionally contain suitable pharmaceutically acceptable nucleation inhibitors, but not limited to, polyvinylpyrrolidone (PVP), crospovidone, hydroxypropyl methyl cellulose (HPMC), polysorbate, phospholipids such as dimyristoylphosphatidyl glycerol (DMPG), disteroylphosphatidylethanolamine (DSPE), 1,2-Distearoyl phosphatidyl ethanolamine methyl-polyethylene glycol conjugate (DSPE-mPEG), or any combination thereof. In one embodiment, polyvinylpyrrolidone may be PVP K12, PVP K17, PVP K25, PVP K30, PVPK 40 or PVP K90.

The inventive pharmaceutical compositions of the present invention may additionally contain a buffering agent, which is used to resist change in pH upon dilution or addition of acid or alkali. Such compounds include, by way of example and without limitation, sodium dihydrogen phosphate monohydrate, disodium hydrogen phosphate anhydrous, acetic acid, sodium acetate, adipic acid, benzoic acid, sodium benzoate, maleic acid, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium tartrate and others known to those of ordinary skill in the art.

The inventive pharmaceutical compositions of the present invention may additionally contain a "tonicity contributing agent" that can be used to adjust the tonicity of the liquid formulation. Suitable tonicity agent include glycerine, lactose, mannitol, dextrose, sodium chloride, sodium sulphate, sorbitol, trehalose, xylitol, sucrose, maltose and others known to those or ordinary skill in the art. In one embodiment, the tonicity of the liquid formulation approximates that of the tonicity of blood or plasma. The amount of tonicity agent may range from about 1 mg/mL to about 20 mg/mL of the composition, preferable from about 5 to about 10 mg/mL.

The inventive pharmaceutical compositions of the present invention may additionally contain a chelating agent selected from the group consisting of ethylene-diaminetetraacetic acid (EDTA), diethylenetriaminepentaacetic acid (DTPA), ethylene glycol-bis(β-aminoethyl ether)-tetra acetic acid (EGTA), N-(hydroxyethyl)ethylene-diaminetriacetic acid (HEDTA), nitrilotriacetic acid (NTA), triethanolamine, 8-hydroxyquinoline, tartaric acid, phosphoric acid, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. More preferably, the chelating agent is selected from the group consisting of EDTA, DTPA, tartaric acid, phosphoric acid, gluconic acid or a pharmaceutically acceptable salt thereof.

The inventive pharmaceutical compositions of the present invention may additionally contain an antioxidant which inhibits oxidation and thus is used to prevent the deterioration of preparations by the oxidative process. Such compounds include by way of example and without limitation, acetone, sodium bisulfate, ascorbic acid, ascorbyl palmitate, citric acid, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and others known to those of ordinary skill in the art. The amount of antioxidant may range from about 0.1 mg/mL to about 50 mg/mL of the composition, and preferably from about 0.5 mg/mL to about 25 mg/mL.

The inventive pharmaceutical compositions of the present invention may additionally contain a preservative selected from the group consisting of ethanol, benzoic acid and the sodium or potassium salts thereof, sorbic acid and the sodium or potassium salts thereof, chlorobutanol, benzyl alcohol, phenyl ethanol, methyl, ethyl, propyl or butyl-p-hydroxybenzoates, phenol, m-cresol, p-chloro-m-cresol, phenylmercury nitrate or benzalkonium chloride.

The inventive pharmaceutical compositions of the present invention may additionally contain pH adjusting agents. The pH adjusting agents are selected from the group consisting of sodium hydroxide, potassium hydroxide, magnesium hydroxide, sodium carbonate, tromethamine, sodium linoleate, sodium oleate, potassium carbonate, potassium linoleate, potassium oleate, and mixtures thereof. In one embodiment, pharmaceutical composition comprising meloxicam can be formulated at any suitable pH. The pH of the pharmaceutical composition preferably ranges from about 5 to about 10, preferably from about 7 to about 9, most preferably about 8 when measured at room temperature. In one embodiment, pharmaceutical composition comprising meloxicam can be formulated by using any suitable pH adjusting agent. In a preferred aspect, it is possible to maintain the pH of the said composition without using a suitable buffering agent.

The inventive pharmaceutical compositions of the present invention may additionally contain anti-foaming agents. The anti-foaming agents are selected from the group consisting of Sodium carboxymethylcellulose, sorbitol, mannitol, polyvinylpyrrolidone (PVP), Polyoxyethylene sorbitan monolaurate or monooleate, polysorbates or Tween 20 and 80, polyoxyethylene/polyoxypropylene/polyoxyethylene copolymer (Pluronic L-62), glycerol polyethylene glycol ricinoleate (Cremophor EL), silicone antifoam (Dimeticone), sorbitan monooleate or monolaurate (Span 20 and 80), propylene glycol; polyethylene glycol 300 (PEG), ethanol, dimethyl acetamide (DMA), glycerol, N-methyl-2-pyrrolidone, and monothioglycerol.

In another embodiment, the stable aqueous parenteral solution comprising meloxicam has a viscosity value between of about 1 cP (centipoise) and 5 cP, for example, 1.5 cP, 2 cP, 2.5 cP, 3 cP, 3.5 cP, 4 cP or 4.5 cP.

In another embodiment, the stable aqueous parenteral solution comprising, meloxicam has an osmolality value of between about 100 mOsm and about 2000 mOsm, for example, about 100 mOsm, about 150 mOsm, about 200 mOsm, about 250 mOsm, about 300 mOsm, about 350 mOsm, about 400 mOsm, about 450 mOsm, about 500 mOsm, about 550 mOsm, about 600 mOsm, about 650 mOsm, about 700 mOsm, about 750 mOsm, about 800 mOsm, about 850 mOsm, about 900 mOsm, about 950 mOsm, about 1000 mOsm, about 1100 mOsm, about 1150 mOsm, about 1200 mOsm, about 1250 mOsm, about 1300 mOsm, about 1350 mOsm, about 1400 mOsm, about 1450 mOsm, about 1500 mOsm, about 1550 mOsm, about 1600 mOsm, about 1650 mOsm, about 1700 mOsm, about 1750 mOsm, about 1800 mOsm, about 1850 mOsm, about 1900 mOsm, about 1950 mOsm, about 2000 mOsm.

In yet another embodiment, the present invention relates to method of reducing moderate to severe post-operative pain as well as opioid requirements in a human subject, the method comprising administering the human subject a solution comprising meloxicam, wherein the composition exhibits rapid onset of action and provides faster relief of pain.

In yet another embodiment, the present invention relates to treatment of osteoarthritis and rheumatoid arthritis in a human subject, the method comprising administering the human subject a solution comprising meloxicam, wherein the composition exhibits rapid onset of action and provides faster relief of pain.

According to a preferred embodiment, the present invention relates to pharmaceutical compositions useful for treating moderate to moderately severe acute pain and/or prescribed for the management of severe pain as an adjunct therapy to opioid analgesics and may allow a reduction in the opioid dose and corresponding adverse events associated with opioid use. When the meloxicam composition of the present invention is formulated into an injectable dosage form and administered to a patient in need thereof, the composition provides a time to first perceptible pain relief. Time to first perceptible pain relief is the time from administration of the drug to the point at which subject first perceives a change in their pain intensity. The time to perceptible pain relief ranges from about less than 1 minute, from about 1 to 30, 2 to 25, 5 to 20, 10 to 20 and 12 to 18 minutes. In other words, an injectable form of the present invention, when administered to a patient in need thereof, provides a time to first perceptible pain relief in about 30, 25, 20, 18, 16, 15, 14, 13, 12, 11, 10, 9, 8, 7, 6, 5, 4, 3, 2, 1 or less than 1 minute.

According to another embodiment, when the stable injectable solution of meloxicam of the present invention is formulated into an injectable dosage form and administered to a subject in need thereof, the composition of the invention provides a time to meaningful pain relief. Time to meaningful pain relief is the time from administration of the drug to the point at which the patient first perceives a meaningful reduction in pain intensity. The time to first meaningful pain relief ranges from about less than 25, from 25 to 300, 75 to 250, 100 to 200, and 115 to 125 minutes. In other words, an injectable form of the present invention, when administered to a patient in need thereof, provides a time to meaningful pain relief in about 300, 275, 250, 225, 200, 195, 185, 175, 165, 155, 150, 125, 100, 75, 50, 25, or less than 25 minutes.

According to yet another embodiment, when the meloxicam solution is formulated into an injectable dosage form and administered to a subject in need thereof, the composition of the invention provides meaningful pain relief for an extended period of time, such as, a period of up to 24 hours. According to other exemplary embodiments, the expended period of time that patients experience meaningful pain relief ranges from about 120 to 1440, 180 to 1320, 240 to 1260, 300 to 1200, 360 to 1140, 480 to 1080, 540 to 1020, 600 to 960, 660 to 900, or 720 to 840 minutes. In other words, an injectable form, of the present invention, when administered to a patient in need thereof, provides a meaningful pain relief for up to about 120, 180, 240, 300, 360, 420, 480, 540, 600, 660, 720, 780, 840, 900, 960, 1020, 1080, 1140, 1200, 1260, 1320, or 1440 minutes. In a preferred embodiment, an exemplary method for treating moderate to moderately severe acute pain comprises administering to a patient in need thereof, an intravenous dosage form comprising 15 mg, 30 mg, or 60 mg, of meloxicam which provides a duration of analgesic effect for up to 1440 minutes (i.e., 24 hours).

According to yet another embodiment, the stable injectable solution of meloxicam suitable for parenteral administration comprising (a) therapeutically effective amount of meloxicam; (b) pharmaceutically acceptable solvent; (c) one or more solubilizers; and (d) optionally, one or more other pharmaceutically acceptable excipients, wherein subject administered with the said composition has shown increased average paw withdrawal latency by 68% when compared with subject administered with reference composition has showed 49% of increased average paw withdrawal latency.

According to yet another embodiment, the present invention provides stable injectable meloxicam solutions at concentrations higher than 5 mg/mL and methods of preparing such solutions. In particular, the present invention provides stable aqueous meloxicam solutions for parenteral administration at concentrations about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL and about 30 mg/mL.

Further in other embodiments, the present invention provides stable injectable meloxicam solutions at concentrations higher than 5 mg/mL and methods of preparing such solutions. In particular, the present invention provides stable aqueous meloxicam solutions for parenteral administration at concentrations about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, about 20 mg/mL, about 20.5 mg/mL, about 21 mg/mL, about 21.5 mg/mL, about 22 mg/mL, about 22.5 mg/mL, about 23 mg/mL, about 23.5 mg/mL, about 24 mg/mL, about 24.5 mg/mL, about 25 mg/mL, about 25.5 mg/mL, about 26 mg/mL, about 26.5 mg/mL, about 27 mg/mL, about 27.5 mg/mL, about 28 mg/mL about 28.5 mg/mL, about 29 mg/mL, about 29.5 mg/mL and about 30 mg/mL.

The unit dose of the meloxicam will be in the range from about 1 to about 200 mg. Exemplary unit dose of meloxicam range from 5 mg to 200 mg, including unit dosages of 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 40 mg, 42.5 mg, 45 mg, 50 mg, 52.5 mg, 55 mg, 57.5 mg, 60 mg, 62.5 mg, 65 mg, 70 mg, 72.5 mg, 75 mg, 80 mg, 82.5 mg, 85 mg, 87.5 mg, 90 mg, 92.5 mg, 95 mg, 97.5 mg, 100 mg, 102.5 mg, 105 mg, 107.5 mg, 110 mg, 112.5 mg, 115 mg, 117.5 mg, 120 mg, 122.5 mg, 125 mg, 127.5 mg, 130 mg, 132.5 mg, 135 mg, 140 mg, 142.5 mg, 145 mg, 150 mg, 152.5 mg, 155 mg, 157.5 mg, 160 mg, 162.5 mg, 165 mg, 170 mg, 172.5 mg, 175 mg, 180 mg, 182.5 mg, 185 mg, 187.5 mg, 190 mg, 192.5 mg, 195 mg, 197.5 mg and 200 mg, wherein unit dose may be packed in vial, ampoule, pre-filled syringe, cartridge or autoinjector.

In certain embodiment, the stable injectable meloxicam solution comprising therapeutically effective amount of meloxicam of the invention may provide value of $T_{max}$ less than 5 hours, for example, less than 4 hours, less than 3 hours, less than 2 hours, less than 1 hour, less than 45 minutes, less than 30 minutes, less than 20 minutes, less than 10 minutes, less than 5 minutes, less than 3 minutes or less than 1 minute or less than 30 seconds, when the solution is administered via subcutaneous or intramuscular route to a human at a meloxicam dose between of 7.5 mg and 60 mg. The solution comprising therapeutically effective amount of meloxicam of the invention provides immediate availability of the entire dose of meloxicam in the blood when the solution is administered via intravenous route to a human.

In further embodiment, the stable injectable meloxicam solution comprising meloxicam of the invention may provide value of $C_{max}$ more than 0.5 μg/mL, for example, more than 0.5 μg/mL, more than 1 μg/mL, more than 1.5 μg/mL, more than 2 μg/mL, more than 2.5 μg/mL, more than 3 μg/mL, more than 3.5 μg/mL, more than 4 μg/mL, more than 4.5 μg/mL, more than 5 μg/mL, more than 5.5 μg/mL, more than 6 μg/mL, more than 6.5 μg/mL, more than 7 μg/mL, more than 7.5 µg/mL, more than 8 µg/mL, more than 8.5 µg/mL, more than 9 µg/mL, more than 9.5 µg/mL, more than 10 µg/mL, more than 15 µg/mL, more than 20 µg/mL, more than 25 µg/mL, more than 30 µg/mL, more than 35 µg/mL, more than 40 µg/mL, more than 45 µg/mL, more than 50 µg/mL, more than 55 µg/mL, more than 60 µg/mL, more than 65 µg/mL, more than 70 µg/mL, more than 75 µg/mL, more than 80 µg/mL, more than 85 µg/mL, more than 90 µg/mL, more than 95 µg/mL, or more than 100 µg/mL, when the solution administered via parenteral route to a subject at a meloxicam dose of between 7.5 mg and 60 mg.

In further embodiment, the stable injectable meloxicam solution comprising meloxicam of the invention may provide value of AUC more than 10 µg*h/mL, more than 20 µg*h/mL, more than 30 µg*h/mL, more than 40 µg*h/mL, more than 50 µg*h/mL, more than 60 µg*h/mL, more than 70 µg*h/mL, more than 80 µg*h/mL, more than 90 µg*h/mL, more than 100 µg*h/mL, more than 150 µg*h/mL, more than 200 µg*h/mL, more than 250 µg*h/mL, more than 300 µg*h/mL, more than 350 µg*h/mL, more than 400 µg*h/mL, more than 450 µg*h/mL, more than 500 µg*h/mL, more than 550 µg*h/mL, more than 600 µg*h/mL, more than 650 µg*h/mL, more than 700 µg*h/mL, more than 750 µg*h/mL, more than 800 µg*h/mL, more than 850 µg*h/mL, more than 900 µg*h/mL, more than 950 µg*h/mL, more than 1000 µg*h/mL, more than 1050 µg*h/mL, more than 1100 µg*h/mL, more than 1150 µg*h/mL, more than 2000 µg*h/mL when the solution is administered via parenteral route to a subject at a meloxicam dose of between 7.5 mg and 60 mg.

In certain embodiments, the stable injectable meloxicam solution suitable for parenteral administration comprises (a) therapeutically effective amount of meloxicam; (b) pharmaceutically acceptable solvent; (c) one or more solubilizers; and (d) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125% or combinations thereof.

In certain embodiments, the stable injectable meloxicam solution suitable for intravenous administration comprises (a) therapeutically effective amount of meloxicam; (b) pharmaceutically acceptable solvent; (c) one or more solubilizers; and (d) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125%; or combinations thereof.

In certain embodiments, the stable injectable meloxicam solution suitable for parenteral administration comprises (a) therapeutically effective amount of meloxicam; (b) pharmaceutically acceptable solvent; (c) one or more solubilizers; (d) one or more nucleation inhibitor; and (e) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125% or combinations thereof.

In certain embodiments, the stable injectable meloxicam solution suitable for intravenous administration comprises (a) therapeutically effective amount of meloxicam; (b) pharmaceutically acceptable solvent; (c) one or more solubilizers; (d) one or more nucleation inhibitor; and (e) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%; (iii) a confidence interval for mean $C_{max}$ between about 80% and about 125%; or combinations thereof.

In further embodiments, the stable injectable meloxicam solution suitable for intravenous administration comprises (a) therapeutically effective amount of meloxicam; (b) pharmaceutically acceptable solvents; (c) one or more solubilizers; and (d) one or more nucleation inhibitors e) optionally, one or more other pharmaceutically acceptable excipients, wherein in said composition upon parenteral administration exhibits bioequivalence to a commercially available reference meloxicam drug product (such as Anjeso®), and wherein said bioequivalence is established by at least one of: (i) a confidence interval for mean $AUC_{0-t}$ between about 80% and about 125%; (ii) a confidence interval for mean $AUC_{0\text{-}infinity}$ between about 80% and about 125%.

In certain embodiments, the invention relates to methods for making a composition, which comprise: (i) dispensing required quantity water for injection; (ii) adding one or more solubilizing agents to form a first solution; (iii) adding meloxicam to the first solution to form a second solution; and (iv) optionally, adjusting the pH of the second solution by adding a suitable acid or base, e.g., hydrochloric acid and/or sodium hydroxide final volume was made with water for injection.

In certain embodiments, the invention relates to methods for making a composition, which comprise: (i) dispensing required quantity water for injection; (ii) adding one or more solubilizing agents to form a first solution; (iii) adding meloxicam to the first solution to form a second solution; (iv) adding one or more solvents and (v) optionally, adjusting the pH of the second solution by adding a suitable acid or base, e.g., hydrochloric acid and/or sodium hydroxide (vi) final volume was made with water for injection.

In certain embodiments, the invention relates to methods for making a composition, which comprise: (i) dispensing required quantity water for injection; (ii) adding one or more solubilizing agents to form a first solution; (iii) adding meloxicam to the first solution to form a second solution; (iv) adding one or more nucleation inhibitor (v) adding one or more solvents and (vi) optionally, adjusting the pH of the second solution by adding a suitable acid or base, e.g., hydrochloric acid and/or sodium hydroxide (vii) final volume was made with water for injection.

Certain embodiments additionally relate to sterilizing the finished products, e.g., aseptic filtration-filling-sealing, terminal sterilization, incorporation of sterilizing agents, irradiation, and/or heating.

Sterilization may be accomplished by any of the conventional methods including aseptic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A pharmaceutically inert gas may be bubbled into the solution to drive out oxygen, which may be selected from nitrogen or carbon dioxide. Preferably, the solution was kept under nitrogen or carbon dioxide sparging until dissolved oxygen less than 10 mg/L in the final solution.

Containers suitable according to the present invention are those known in the art. They include vials, cartridges, pre-filled syringes, auto-injectors, infusion bags, bottles and ampoule presentations. Containers may be fabricated from glass or from polymeric materials. Suitable containers should be of a size sufficient to hold one or more doses of meloxicam.

The present invention provides for stable injectable meloxicam solution in single-dose and/or multi-dose compositions. In some embodiments, the composition may be contained in vials. In some embodiments, the vials may be made from clear glass, amber glass, or plastic. In some embodiments, the vials or pre-filled syringes may be in the range of about 0.1 mL to 100 mL in volume, preferably in the range of about 1 mL to 50 mL, more preferably in the range of about 1 mL to 10 mL, and most preferably in the range of about 1 mL to 5 mL. In some embodiments, the composition may exist in a 5 mL vial. In some embodiments, the 5 mL vial may be a single-dose formulation. In some embodiments, the 10 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days.

In another embodiment the vial, ampoule or syringe is dimensioned so as to have a nominal maximum fill volume of between about 1 mL and about 10 mL. In certain embodiments the nominal maximum fill volume is between about 1 mL and about 5 mL. In certain embodiments the nominal maximum fill volume is about 1 mL or about 2 mL.

The polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition, crystal zenith (CZ) resin containers and similar resins can be used as rigid containers and syringes.

A ready-to-use pre-filled syringe comprising stable injectable meloxicam solution according to the invention will be advantageous, as compared to vials or ampoules. A pre-filled syringe fabricated from a polymer will not only be convenient for handling, storage and administration, but will also minimize mixing or dosing errors. The pre-filled syringe according to the invention may also include single use auto injectors and reusable auto injectors. The pre-filled syringe contains various constituent parts, for example, a sterile clear USP Type-I siliconized glass syringe barrel (1 mL, cut flange with a gauge (29 size), hypodermic needle (½ inch) fitted with rigid needle shield and laminated bromobutyl plunger stopper for the barrel.

In another embodiment, the present invention provides a kit comprising an auto injector which contains a pre-filled syringe (a pre-filled syringe assembled/placed in the auto injector). The autoinjector may be integrated with a needle stick protection feature and holds a pre-filled syringe containing a single dose, whereby the entire deliverable volume is expelled.

The stable injectable meloxicam solution preparations as described herein may further comprise effective amounts of one or more other therapeutically active ingredient. Suitable other active ingredients used in some of the embodiments of present disclosure include, but are not limited to, Nonsteroidal anti-inflammatory drugs (NSAIDs), opioids, corticosteroids, anaesthetic agents or mixtures thereof.

Stability: As used herein, the term "stable" is defined as no more than about 5% loss of meloxicam under typical commercial storage conditions. In certain embodiments, the compositions of the present invention will have no more than about 2% loss of meloxicam, more preferably, no more than about 1% loss of meloxicam, under typical commercial storage conditions. The composition retains at least about 95% of the potency of meloxicam after storing the composition at 40° C. and 75% relative humidity (herein after mentioned as RH) for at least three months. In certain aspects, the term "stable" refers to chemical stability, wherein not more than 1.5% w/w of total related substances are formed on storage at accelerated conditions of stability at 40° C. and 75% RH or at 25° C. and 60% RH or 2-8° C. for a period of at least six months or to the extent necessary for use of the composition.

In another embodiment, the stable injectable meloxicam solution comprising meloxicam, may have a shelf life after opening of 14 days or more.

In certain embodiments, the inventive pharmaceutical compositions according to the invention is stable for at least 3 months at 25° C. and 60% RH. In certain embodiments, the composition according to the invention is stable for at least 3 months at 40° C. and 75% RH. In certain embodiments, the composition according to the invention is stable for at least 24 months when stored under room temperature.

In particular, the Impurity-B (i.e., 2-Amino-5-methylthiazole), formed due to hydrolytic degradation, may be monitored. The structure of meloxicam impurity-B is shown below:

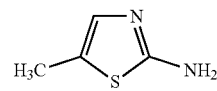

In certain embodiments, the inventive pharmaceutical composition according to the invention has a level of Impurity-B that is less than 2% as measured by HPLC, preferably less than 1% as measured by HPLC, and most preferably less than 0.5% as measured by HPLC.

In particular, the oxalate impurity (i.e., 4-Hydroxy-2-(methyl-thio)-pyrimidine-5-carboxylic acid) formed due to oxidative degradation, may be monitored. The structure of oxalate impurity is shown below:

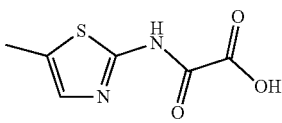

In certain embodiments, the inventive pharmaceutical composition according to the invention has a level of oxalate impurity that is less than 2% as measured by HPLC, preferably less than 1% as measured by HPLC, and most preferably less than 0.5% as measured by HPLC.

In an embodiment, inventive pharmaceutical compositions of the present application were found to remain in solution, without any recrystallization or precipitation, when stored for 6 months at 2-8° C., 25° C./60% RH condition or 40° C./75% RH conditions.

In an embodiment, the invention relates to stable injectable meloxicam solution intended for intravenous administration comprising about meloxicam and solubilizers, wherein the solution is stable for at least 6 months at 40° C./75% RH condition.

In another embodiment, the invention relates to stable injectable meloxicam solution comprising meloxicam, wherein the solution is stable for at least 3 months at 2° C. to 8° C.

In another embodiment, the stable injectable meloxicam solution comprising meloxicam is dear (free of any crystals/precipitates) by visual, inspection after storage for at least 1 month, for example, 2 months, 3 months, 6 months, 12 months, 18 months, or 24 months, at controlled room temperature. The solution of the present invention provides value of absorbance not more than 1, for example, not more then 0.75, 0.5, 0.4, 0.3, 0.2, 0.1 or 0.05 and value of % transmittance not less than 90%, for example, not less than 95%, 96%, 97%, 98%, 99%, 99.5% or 99.9%.

In another embodiment, the stable injectable meloxicam solution comprising meloxicam does not contain 4-Hydroxy-2-methyl-2H-1,2-benzothiazine-3-carboxylic acid ethyl ester 1,1-dioxide (also known as Impurity-A) more than 0.5%, for example, 0.4%, 0.3%, 0.2%, 0.1% or 0.05%, by weight of meloxicam, as measured by HPLC.

In another embodiment, the stable injectable meloxicam solution comprising meloxicam does not contain 2-amino-5-methyl-thiazole (also known as Impurity-B) more than 0.5%, for example, 0.4%, 0.3%, 0.2%, 0.1% or 0.05%, by weight of meloxicam, as measured by HPLC.

In another embodiment, the stable injectable meloxicam solution comprising meloxicam does not contain Methyl-4-hydroxy-2-methyl-2H-1,2-benzothiazine-3-carboxylate-1,1-Dioxide (also known as Impurity-D) more than 0.5%, for example, 0.4%, 0.3%, 0.2%, 0.1% or 0.05%, by weight of meloxicam, as measured by HPLC.

In another embodiment, the stable injectable meloxicam solution comprising meloxicam does not contain N-(3,5-dimethylthiazol-2-(3H)-ylidene)-4-hydroxy-2-methyl-2H-benzo[e][1,2]thiazine-3-carboxamide-1,1-dioxide (also known as Impurity E) more than 0.5%, for example, 0.4%, 0.3%, 0.2%, 0.1% or 0.05%, by weight of meloxicam, as measured by HPLC.

In another embodiment, the stable injectable meloxicam solution comprising meloxicam does not contain N-(3-Ethyl-5-methylthiazol-2(3H)-ylidene)-4-hydroxy-2-methyl-2H-benzo[e][1,2]thiazine-3-carboxamide-1-dioxide (Ethyl meloxicam impurity) more than 0.5%, for example, 0.4%, 0.3%, 0.2%, 0.1% or 0.05%, by weight of meloxicam, as measured by HPLC.

In another embodiment, the stable injectable meloxicam solution comprising meloxicam does not contain 2-(diazinyl-sulfonyl)-N-methylaniline-oxide (Meloxicam diazinylsulfonyl Impurity) more than 1%, for example, 0.8%, 0.5%, 0.4%, 0.3%, 0.2%, 0.1% or 0.055% by weight of meloxicam, as measured by HPLC.

In another embodiment of the invention, there is provided stable injectable meloxicam solution comprising meloxicam, wherein the solution does not contain single maximum unknown impurity more than 1% and/or does not contain total impurities more than 3% (for example, not more than 2%, 1%, or 0.5%) after storage for more than 2 months, for example, for 3 months, for 6 months, for 12 months, for 18 months, for 24 months or for 36 months when stored at (i) 2-8° C. temperature or at (ii) 25±2° C. temperature and 60±5% RH or at (iii) 40±2° C. and 75±5% RH. The parenteral solution comprising meloxicam of the present invention does not form any precipitate and remains physically stable after storage for more than 2 months, for example, for 3 months, for 6 months, for 12 months, for 18 months, for 24 months or for 36 months when stored at 2-8° C. temperature or at 25±2° C. temperature and 60±5% RH.

In another embodiment, the stable injectable meloxicam solution comprising meloxicam has a shelf-life in the sealed original packaging may be 1 month or more, in particular between 1 month and 36 months, but at least between 1 month and 24 months, preferably between 1 month and 12 months.

Dosage and Administration: The inventive pharmaceutical compositions as described herein may be used in treating moderate-to-severe pain in which therapeutically effective amount of meloxicam is administered to a human subject.

For administration to human subjects, the inventive pharmaceutical compositions comprise an effective dosage amount of meloxicam. The formulation may be prepared using conventional methods, for example, depending on the subject to be treated, the mode of administration, and the type of treatment desired (e.g., prevention, prophylaxis, or therapy).

Preferably, the present application relates to method for managing or treating or alleviating moderate-to-severe pain, alone or in combination with non-NSAID analgesics, the method comprising administering the human subject, a pharmaceutical composition comprising meloxicam.

More preferably, the present application relates to method for managing or treating or alleviating moderate-to-severe pain alone or in combination with non-NSAID analgesics not limiting to opioids or local anaesthetics, the method comprising administering the human subject, a pharmaceutical composition comprising meloxicam.

In another aspect, the present invention relates to method for managing or treating or alleviating the signs and symptoms of osteoarthritis, rheumatoid arthritis and pauciarticular or polyarticular course juvenile rheumatoid arthritis (JRA)/juvenile idiopathic arthritis (JIA) in the human subject, wherein the method comprises administering the human subject, a pharmaceutical composition comprising meloxicam.

Determination of meloxicam optimal dosage may require individual titration. Therapy may be started at a low dosage, and increase gradually until optimum effect is achieved (e.g., usually between 5-40 mg daily). In certain embodiments, 1-20 mL of meloxicam solution may be administered intravenously to achieve optimum effect, preferably 1-10 mL may be administered to achieve optimum effect.

In an embodiment, the present invention relates to preventing or managing or treating or alleviating moderate-tosevere pain or mild to severe pain or post-surgical pain in a human subject, the method comprising administering 30 mg of meloxicam solution once daily, as intravenous bolus injection over 15 seconds to a human subject.

In one embodiment of the method as disclosed herein, the intravenous dose (including a bolus dose) of meloxicam is administered to the patient over the course of about 1 to about 60 seconds, including all values and sub-ranges there between. The IV dose of meloxicam may be administered to patient in about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 second, about 20 seconds, about 21 second, about 22 seconds, about 23 seconds, about 24 seconds, about 25 second, about 26 seconds, about 27 seconds, about 28 seconds, about 29 second, about 30 seconds, about 31 second, about 32 seconds, about 33 seconds, about 34 seconds, about 35 second, about 36 seconds, about 37 seconds, about 38 seconds, about 39 second, about 40 seconds, about 41 second, about 42 seconds, about 43 seconds, about 44 seconds, about 45 second, about 46 seconds, about 47 seconds, about 48 seconds, about 49 second, about 50 seconds, about 51 second, about 52 seconds, about 53 seconds, about 54 seconds, about 55 second, about 56 seconds, about 57 seconds, about 58 seconds, about 59 second, or about 60 seconds, or any ranges between these values.

For example, in some embodiments, the IV dose (including a bolus dose) of meloxicam is administered to the patient over the course of about 5 to about 45 seconds. In other embodiments, the IV dose of meloxicam is administered to the patient over the course of about 10 to about 40 seconds. In still other embodiments, the IV dose of meloxicam is administered to the patient over the course of about 15 to about 35 seconds. In some embodiments, the IV dose of meloxicam is administered to the patient over the course of about 10 to about 30 seconds. In certain embodiments, the IV dose of meloxicam is administered to the patient over the course of about 15 to about 30 seconds. In one embodiment, the IV dose of meloxicam is administered to the patient over about 15 seconds.

In one embodiment, the dose of meloxicam is in the range of from about 5 mg to about 200 mg. In some embodiments, the dose of meloxicam is in the range of from about 15 mg to about 180 mg. In some embodiments, the dose of meloxicam is in the range of from about 15 mg to about 100 mg. In other embodiments, the dose of meloxicam is in the range of from about 15 mg to about 80 mg. In some embodiments, the dose of meloxicam is in the range of from about 20 mg to about 70 mg. In some embodiments, the dose of meloxicam is in the range of from about 30 mg to about 60 mg. In some embodiments, the dose of meloxicam is about 30 mg. In another embodiment, the dose of meloxicam is about 60 mg.

In some embodiments, the methods comprise administering stable injectable meloxicam solution to a subject at about 12 hours, at about 18 hours, at about 24 hours, at about 36 hours, at about 48 hours, at about 54 hours, at about 72 hours, at about 96 hours, at about 5 days, at about 6 days, and so forth subsequent to the first dose of meloxicam administered to the subject.

In one embodiment, the methods disclosed herein comprise administering to the patient a dose of meloxicam intravenously, wherein the meloxicam is at a dose of about 30 mg. In some embodiments, the methods disclosed herein comprise administering to the patient a dose of meloxicam intravenously, wherein the meloxicam is at a concentration of about 7.5 mg/mL or 30 mg/mL. In one embodiment, the intravenous dose is a bolus dose.

In one embodiment of the method as disclosed herein, the dose of meloxicam is administered after the patient has undergone a surgical procedure. In one embodiment, the surgical procedure is an open surgical procedure. In another embodiment, the surgical procedure is a laparoscopic surgical procedure. In other embodiments, the surgical procedure was performed on hard tissue. In some embodiments, the surgical procedure was performed on soft tissue.

In an embodiment, the present invention relates to method of treating signs and symptoms of polyarticular course juvenile rheumatoid arthritis (JRA)/juvenile idiopathic arthritis (JIA) in patients of age less than 18 years with a dose of meloxicam ranging from 0.1 mg/kg a day to 0.2 mg/kg a day.

In certain aspects, the inventive pharmaceutical compositions described herein may be used to treat adults and adolescents (e.g., about 13-17 years). In certain aspects, the pharmaceutical compositions described herein may be used as monotherapy or as adjunctive therapy. For example, additional active agents may be used in adjunctive therapy with meloxicam, such as opioid medications (e.g., morphine, hydromorphone, etc.).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

The inventive pharmaceutical compositions of the present disclosure provide for a non-oral, easy-to-administer option for patients having moderate-to-severe pain.

General HPLC procedure: As explained in detail below, the following HPLC procedure can be used to detect and quantify impurities of baclofen. The materials and general conditions are listed below:

TABLE 1

Related substances identification by HPLC Chromatographic conditions

| | |
|---|---|
| Instrument | HPLC with Dual wavelength detector |
| Column | Inert Sustain C18, 250 mm × 4.6 mm, 3μ (Cat. No.: 5020-07446) |
| Pump mode | Gradient |
| Flow rate | 0.8 mL/minute |
| Detector wavelength | 260 nm and 350 nm with dual wavelength detector |
| Column oven temperature | 40° C. |
| Sample cooler temperature | 25° C. |
| Injection volume | 10 μL |
| Run time | 60 minutes |
| Preparation of Mobile phase-A | Prepare a mixture of Buffer* and organic modifier* in the ratio of 70:30 (% v/v) and degas for about 10 minutes. |
| Preparation of Mobile phase-B | Prepare a mixture of Buffer and organic modifier in the ratio of 30:70 (% v/v) and degas for about 10 minutes. |
| *Preparation of buffer | Weigh about 1.0 g of Potassium dihydrogen phosphate and dissolve in 1000 mL of water. Adjust the pH of the solution to 6.00 ± 0.05 with 1N Sodium hydroxide preparation. Filter the buffer through 0.45μ Durapore PVDF filter (Millipore). |

TABLE 1-continued

Related substances identification
by HPLC Chromatographic conditions

| | |
|---|---|
| *Preparation of organic modifier | Mix Methanol, Acetonitrile and Water in the ratio of 70:20:10 respectively. |

TABLE 2

Gradient program

| Time (min) | % Mobile phase-A | % Mobile phase-B |
|---|---|---|
| 0.01 | 100 | 0 |
| 20 | 100 | 0 |
| 35 | 0 | 100 |
| 50 | 0 | 100 |
| 52 | 100 | 0 |
| 60 | 100 | 0 |

TABLE 3

Assay of Meloxicam injection by HPLC Chromatographic conditions

| | |
|---|---|
| Instrument | HPLC system equipped with UV/PDA-detector, binary/quaternary gradient pump, auto injector and suitable software |
| Column | Agilent Zorbax Eclipse XDB C18, 5μ (4.6 mm ID, × 150 mm) |
| Pump mode | Gradient |
| Flow rate | 1.0 mL/minute |
| Detector wavelength | 350 nm |
| Column oven temperature | 40° C. |
| Sample cooler temperature | 25° C. |
| Injection volume | 10 μL |
| Run time | 25 minutes |
| Preparation of Mobile phase-A | Prepare a mixture of Buffer** and organic modifier in the ratio of 70:30 (% v/v) and degas it for about 10 minutes. |
| Preparation of Mobile phase-B | Prepare a mixture of Buffer and organic modifier in the ratio of 30:70 (% v/v) and degas it for about 10 minutes. |
| **Preparation of Buffer | Weigh 1.36 g of Potassium dihydrogen phosphate and dissolve in 1000 mL of water. To this add 2 mL of Triethylamine and mix well. Adjust the pH of the solution to 7.00 ± 0.05 with dilute orthophosphoric acid. Filter the buffer through 0.45μ Durapore PVDF filter (Millipore). |

TABLE 4

Gradient program

| Time (minutes) | % Mobile Phase-A | % Mobile Phase-B |
|---|---|---|
| 0.01 | 100 | 0 |
| 12 | 0 | 100 |
| 17 | 0 | 100 |
| 18 | 100 | 0 |
| 25 | 100 | 0 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Meloxicam solution having composition was set forth in Table 5.

TABLE 5

| Ingredients | Composition A (Batch size - 200 mL) | Composition B (Batch size - 250 mL) |
|---|---|---|
| Meloxicam | 7.5 mg | 15 mg |
| Meglumine | 25 mg | 25 mg |
| Water for injection | q.s. to 1 mL | q.s. to 1 mL |
| Hydrochloric acid | q.s. for adjusting pH to 8 | q.s. for adjusting pH to 8 |

Manufacturing procedure of Composition A and B: About 60% required quantity of water for injection was taken in two beakers (Beaker 1 and 2). 5 and 6.25 grams of meglumine was added to the Beaker 1 and 2 respectively and stirred for about 5-10 minutes at 500 RPM to obtain clear solutions. 1.5 and 3.75 grams of meloxicam was added to the clear solutions of Beaker 1 and 2 respectively and stirred continuously for another 60-80 minutes at 800-900 RPM. Sufficient quantities of water for injection were added to make up volume to 200 mL in Beaker 1 and 250 mL in Beaker 2. pH of final solutions was adjusted to 8 using 0.1N hydrochloric acid. Final solution in Beaker 1 and 2 were Composition A and B respectively.

Stability data of Composition A and B were set forth in Table 6

TABLE 6

| | Composition A | | | | Composition B | | |
|---|---|---|---|---|---|---|---|
| Storage Condition | — | 25° C./ 60% RH | 40° C./ 75% RH | 2-8° C. | — | 25° C./ 60% RH | 40° C./ 75% RH |
| Duration | Initial | 6 months | | 3 months | Initial | 6 months | |
| Visual observation of solution | Clear | Clear | Clear | Clear | Clear | Clear | Clear |
| pH | 8.01 | 7.89 | 7.67 | 8.07 | 8.41 | 8.48 | 8.45 |
| Assay | 103.2 | 102.8 | 103.1 | 101.9 | 99.1 | 101.1 | 100.6 |
| Osmolality | — | 237 | 238 | 238 | 232 | 218 | 219 |

TABLE 6-continued

|  | Composition A | | | | Composition B | | |
|---|---|---|---|---|---|---|---|
|  | Impurities (% w/w) | | | | | | |
| Impurity-B | 0.006 | 0.037 | 0.205 | 0.023 | ND | 0.026 | 0.126 |
| Unspecified impurity (at RRT) | 0.019 (1.580) | 0.011 (0.85) | ND | 0.017 (1.69) | 0.015 (1.716) | 0.043 | 0.039 (1.65) |
| Total impurities | 0.04 | 0.048 | 0.205 | 0.06 | 0.042 | 0.102 | 0.21 |

Example 2

Meloxicam solution having composition was set forth in Table 7.

TABLE 7

| Ingredients | Composition C (Batch size - 150 mL) |
|---|---|
| Meloxicam | 25 mg |
| Meglumine | 45 mg |
| Ethylenediaminetetraacetic acid (EDTA) | 0.20 mg |
| Water for injection | q.s. to 1 mL |
| Hydrochloric acid (1N) | q.s. for adjusting pH to 8 |

Manufacturing procedure of Composition C: About 60% required quantity of water for injection was taken in a beaker. 6.75 grams of meglumine and 0.03 grams of EDTA were added to the beaker and stirred for about 5-10 minutes at 500 RPM to obtain a clear solution. 3.75 grams of meloxicam was added to the clear solution and stirred continuously for another 60-80 minutes at 800-900 RPM. Sufficient quantity of water for injection was added to make up volume to 150 mL. pH of final solutions was adjusted to 8 using 0.1N hydrochloric acid.

Samples of Composition C was stored at 25° C./60% RH and 40° C./75% RH for 3 months, particles were observed after storing at 25° C./60%RH and 40° C./75% RH for 3 months.

Stability data of Composition C was set forth in Table 8

TABLE 8

| | Composition C | | |
|---|---|---|---|
| | Storage Condition | | |
| Duration | Initial | 25° C./ 60% RH 3 months | 40° C./ 75% RH 3 months |
| Visual observation of solution | Clear | Particles observed | Particles observed |
| pH | 8.65 | 8.62 | 8.64 |
| Assay | 101.1 | 103.7 | 100.3 |
| Osmolality | 383 | 387 | 389 |
| | Impurities (% w/w) | | |
| Impurity-B | ND | 0.031 | 0.165 |
| Unspecified impurity (at RRT) | 0.017 (1.718) | 0.019 (0.446) | 0.530 (0.430) |
| Total impurities | 0.041 | 0.073 | 0.275 |

Example 3

Meloxicam solution having composition was set forth in Table 9.

TABLE 9

| Ingredients | Composition D (Batch size - 250 mL) |
|---|---|
| Meloxicam | 6 mg |
| L-Arginine | 5 mg |
| HP-β-CD | 90 mg |
| Water for injection | q.s. to 1 mL |
| Hydrochloric acid | q.s. for adjusting pH to 8 |

Manufacturing procedure of Composition D: About 125 mL of water for injection was taken in a beaker. 1.25 grams of L-Arginine was added to the beaker and stirred for about 15-20 minutes at 500 RPM to obtain a clear solution. 22.50 grams of HP-β-CD was added to the clear solution and stirred for about 5-10 minutes at 500 RPM to obtain a clear solution. 1.50 grams of meloxicam was added to the obtained solution and continued stirring for another 40-50 minutes at 800-900 RPM. Sufficient quantity of water for injection was added to make up volume to 250 mL. pH of final solutions was adjusted to 8 using 0.1 N hydrochloric acid.

Samples of Composition D was stored at 2-8° C. for 3 months, 25° C./60% RH and 40° C./75% RH for 6 months. Meloxicam solutions were clear without any particles after storing at 25° C./60% RH and 40° C./75% RH for 6 months, and at 2-8° C. for 3 months.

Stability data of Composition D was set forth in Table 10

TABLE 10

| | Composition D | | | | | |
|---|---|---|---|---|---|---|
| Storage Condition | — | 25° C./60% RH | | 40° C./75% RH | | 2-8° C. |
| Storage duration | Initial | 3 months | 6 months | 3 months | 6 months | 3 months |
| Visual observation of solution | Clear | Clear | Clear | Clear | Clear | Clear |

TABLE 10-continued

| | | | Composition D | | | |
|---|---|---|---|---|---|---|
| pH | 8.1 | 7.77 | 8.05 | 8.06 | 7.82 | 8.04 |
| Assay | 101.6 | 102 | 102.0 | 102.3 | 99.8 | 102.4 |
| Osmolality | 113 | 116 | 113 | 117 | 121 | 117 |
| | | | Impurities (% w/w) | | | |
| Impurity-B | 0.006 | 0.015 | 0.042 | 0.105 | 0.358 | 0.016 |
| Unspecified impurity (at RRT) | 0.021 | 0.019 | 0.002 | 0.022 | 0.004 | 0.025 |
| Total impurities | 0.04 | 0.07 | 0.044 | 0.15 | 0.362 | 0.07 |

Example 4

Meloxicam solution having composition was set forth in Table 11.

TABLE 11

| Ingredients | Composition E (Batch size - 100 mL) | Composition F (Batch size -100 mL) |
|---|---|---|
| Meloxicam | 10 mg | 30 mg |
| Sodium dihydrogen phosphate monohydrate | 3.4 mg | — |
| Disodium hydrogen phosphate anhydrous | 10.5 mg | — |
| PEG-400 | 400 mg | 180 mg |
| Meglumine | — | 20 mg |
| Hydrochloric acid (1N) | — | q.s. for adjusting pH to 8.3 |
| Water for Injection | q.s. to 1 mL | q.s. to 1 mL |

Manufacturing procedure of Composition E and F: About 60% required quantity of water for injection was taken in two beakers (Beaker-1 and Beaker-2). 0.34 grams of sodium dihydrogen phosphate monohydrate was added to Beaker-1 and stirred to obtain a clear solution. 1.05 grams of disodium hydrogen phosphate anhydrous was added to clear solution of Beaker-1 and stirred continuously to obtain a clear solution. 2 grams of meglumine was added to Beaker-2 and stirred for 5-10 minutes at 500 RPM to get a clear solution. 40 & 18 grams of PEG-400 was added to Beaker-1 and Beaker-2 respectively and stirred at 500 RPM for almost 15 minutes to get a clear solution. 1 gm & 3 gm of meloxicam was added to each Beaker-1 and Beaker-2 respectively and stirred at 800-900 RPM for 60-80 minutes. Sufficient quantities of water for injection was added to Beaker-1 and 2 to make up volume to 100 mL. pH of Composition E was 7. pH of Composition F was adjusted to 8.3 by adding sufficient quantity of 1N HCl.

Samples of Composition E was stored at 2-8° C., 25° C./60% RH and 40° C./75% RH for 3 months. Meloxicam solutions were clear without any particles after storing at 25° C./60% RH and 40° C./75% RH for 3 months. A dull white jelly like substance observed at the bottom of solution when stored at 2-8° C. for 3 months.

Stability data of Composition E was set forth in Table 12

TABLE 12

| | Composition E | | | |
|---|---|---|---|---|
| | Storage Condition | | | |
| | — | 25° C./ 60% RH | 40° C./ 75% RH | 2-8° C. |
| Storage duration | Initial | | 3 months | |
| Visual observation of solution | Clear | Clear | Clear | A dull white jelly like substance observed at the bottom |
| pH | 7.25 | 7.39 | 7.43 | 7.33 |
| Assay | 100.5 | 100.1 | 100.1 | 100.9 |
| | Impurities (% w/w) | | | |
| Impurity-B | 0.027 | 0.154 | 0.446 | 0.016 |
| Unspecified Impurity (at RRT) | 0.024 (0.681) | 0.022 (0.62) | 0.024 (0.98) | 0.013 (1.69) |
| Total impurities | 0.117 | 0.234 | 0.538 | 0.046 |

Example 5

Meloxicam solution having composition was set forth in Table 13.

TABLE 13

| Ingredients | Composition G (Batch size - 100 mL) | Composition H (Batch size - 100 mL) |
|---|---|---|
| Meloxicam | 30.0 mg | 30.0 mg |
| Diethanolamine | 150.0 mg | 150.0 mg |
| Meglumine | 25.0 mg | — |
| Hydrochloric acid (1N) | q.s. for adjusting pH to 8 | q.s. for adjusting pH to 8 |
| Water for Injection | q.s. to 1 mL | q.s. to 1 mL |

Manufacturing procedure of Composition G and H: About 70% required quantity of water for injection was taken in two beakers (Beaker-1 & 2). 15 g of diethanolamine was added to each of the Beaker-1 and Beaker-2; 2.5 g of meglumine was added to Beaker-2 and were then stirred to obtain clear solutions. 3 g of meloxicam was added to the clear solutions of each beaker and stirred continuously for another 60-80 minutes at 800-900 RPM. Sufficient quantity of water for injection was added to Beaker-1 and 2 to make up volumes to 100 mL. pH of solutions was adjusted to 8 using 1N hydrochloric acid.

Example 6

Meloxicam solution having composition was set forth in Table 14.

TABLE 14

| | Composition | | | | | |
|---|---|---|---|---|---|---|
| Ingredients | I | J | K | L | M | N |
| Batch size | 150 mL | 150 mL | 100 mL | 100 mL | 100 mL | 50 mL |
| Meloxicam | 30.0 mg | 30.0 mg | 30.0 mg | 20.0 mg | 15.0 mg | 30 mg |
| HP-β-CD | 190.0 mg | 220.0 mg | 150.0 mg | 100.0 mg | 100.0 mg | 150 mg |
| Meglumine | 20.0 mg | 20.0 mg | 20.0 mg | 20.0 mg | 20.0 mg | 20 mg |
| TRIS | — | — | — | — | — | 12 mg |
| HCL (1N) | | | q.s. for adjusting pH to 8 | | | |
| Water for Injection | q.s. to 1 mL | q.s. to 1 mL | q.s. to 1 mL | q.s. to 1 mL | q.s. to 1 mL | q.s. to 1 mL |

Manufacturing procedure of Composition I, J, K, L, M and N: About 70% quantity of water for injection was heated to 50° C.-60° C. in was taken in six beakers (Beaker-1, 2, 3, 4, 5 & 6). 0.6 g of TRIS was added to Beaker-6 and stirred to obtain clear solution. Specified amount of meglumine was added to water for injection at 50° C.-60° C. and stirred continuously for 5 minutes at 500±50 RPM to obtain clear meglumine solution. Specified quantity of HP-β-CD was added to the meglumine solution and mixed continuously at temperature 50-60° C. for next 60 minutes at 500±50 RPM to obtain clear HP-β-CD solution. Specified quantity of meloxicam was added to the HP-β-CD solution and mixed continuously at temperature 50-60° C. for the next 60 minutes at 500±50 RPM to obtain clear meloxicam solution was kept for cooling to room temperature under continuous stirring. The remaining amount of water for injection was added to the meloxicam solution to prepare final solution. pH of the final solutions was adjusted to 8 with 1N hydrochloric acid.

Samples of Composition I and J were stored for 3 months at 25° C./60% RH and at 40° C./75% RH. Meloxicam solutions were clear without any particles after storing at 25° C./60% RH and at 40° C./75% RH for 3 months.

Stability data of Composition I and J was set forth in Table 15.

TABLE 15

| | Composition I | | | Composition J | | |
|---|---|---|---|---|---|---|
| Storage Condition | Initial | 25°C./ 60% RH | 40°C./ 75% RH | Initial | 25°C./ 60% RH | 40°C./ 75% RH |
| Storage duration | | 3 months | | | 3 months | |

TABLE 15-continued

|  | Composition I | | | | Composition J | |
|---|---|---|---|---|---|---|
| Visual observation of solution | Clear solution | | | | Clear solution | |
| pH | 8.05 | 8.11 | 8.10 | 8.06 | 8.05 | 8.06 |
| Osmolality | 338 | 350 | 337 | 367 | 352 | 360 |
| Assay | 101.1 | 104.4 | 104.3 | 97.8 | 97.2 | 96.1 |
| Impurities (% w/w) | | | | | | |
| Impurity-B | ND | 0.020 | 0.125 | ND | 0.031 | 0.2 |
| Unspecified Impurity (at RRT) | 0.011 (0.793) | 0.015 (1.68) | 0.015 (1.68) | 0.014 (0.794) | 0.019 (1.68) | 0.012 (1.68) |
| Total impurities | 0.03 | 0.06 | 0.16 | 0.02 | 0.07 | 0.24 |

Samples of Composition L and M were stored for 7 days at 60° C. Meloxicam solutions were clear without any particles after storing at 60° C. for 7 days.

Stability data of Composition L and M was set forth in Table 16.

TABLE 16

|  | Composition | |
|---|---|---|
|  | L | M |
| Storage Condition | 60° C. | |
| Storage duration | 7 days | |
| Visual observation of solution | Clear | Clear |
| pH | 8.18 | 8 |
| Assay | 100.5 | 98.5 |
| Osmolality | 255 | 251 |

TABLE 16-continued

|  | Composition | |
|---|---|---|
|  | L | M |
| Impurities (% w/w) | | |
| Impurity-B | 0.119 | 0.094 |
| Unspecified Impurity (at RRT) | 0.016 (0.80) | 0.014 (0.80) |
| Total impurities | 0.17 | 0.13 |

Samples of Composition K and N were stored at 60° C. for 7 days and for 6 months at 25° C./60% RH and at 40° C./75% RH. Meloxicam solutions were clear without any particles after storing at 60° C. for 7 days and at 25° C./60% RH for 6 months. Tiny particles were observed in Composition K and N when stored at 40° C./75% RH for 6 months Stability data of Composition K and N was set forth in Table 17.

TABLE 17

|  | Composition K | | | | Composition N | | | |
|---|---|---|---|---|---|---|---|---|
| Storage Condition | Initial | 60° C. | 25° C./ 60% RH | 40° C./ 75% RH | Initial | 60° C. | 25° C./ 60% RH | 40° C./ 75% RH |
| Storage duration |  | 7 days | 6 months | | | 7 days | 6 months | |
| Visual observation of solution | Clear | Clear | Clear | Tiny particles | Clear | Clear | Clear | Tiny particles |
| pH | 7.87 | 8.37 | 7.76 | 7.43 | 8.02 | 8.07 | 8.02 | 8.03 |
| Assay | 98.7 | 99.5 | 99.8 | 99.8 | 100.6 | 98.7 | 99.9 | 99.1 |
| Osmolality | 290 | 271 | 290 | 292 | 477 | 464 | 464 | 473 |
| Impurities (% w/w) | | | | | | | | |
| Impurity-B | 0.005 | 0.206 | 0.035 | 0.386 | 0.006 | 0.109 | 0.045 | 0.316 |
| Unspecified Impurity (at RRT) | 0.019 (1.69) | 0.017 (1.69) | 0.013 (1.71) | 0.022 (0.44) | 0.019 (0.80) | 0.015 (1.69) | 0.012 (1.71) | 0.020 (0.44) |
| Total impurities | 0.05 | 0.25 | 0.08 | 0.46 | 0.06 | 0.15 | 0.09 | 0.39 |

Example 7

Animal Study: Evaluation of Efficacy of Meloxicam Compositions in Acute Post-operative Pain (Brennan) Model in Sprague Dawley Rats.

The analgesic efficacy of Composition K was studied in comparison with Anjeso® and ketorolac tromethamine drug products in a rat acute post-operative pain model at a dose of 3 mg/kg administered by intravenous route. Composition K has shown better trend compared to Anjeso® in terms of maximum efficacy and rate of analgesia development. Composition K have shown significant extended efficacy compared to Anjeso®.

Meloxicam compositions (Anjeso® & Composition K) & ketorolac drug products were tested in an acute post-operative (Brennan) pain model in rats after intravenous administration. Average paw withdrawal latency & mechanical hyperalgesia (pain assessment) parameters were assessed in rats after intravenous administration of vehicle (0.9% saline), ketorolac tromethamine (3 mg/kg), Anjeso® (3 mg/kg), Composition K (3 mg/kg). Evaluations began 30 minutes following surgery, and were continued for 240 minutes.

Prior to surgery, mean paw withdrawal latency showed no statistical difference between any of the treatment groups. Mean paw withdrawal latency was between 8.6 to 8.9 across all the treatment groups. After surgical incision all animals demonstrated increased mechanical sensitivity with paw withdrawal latency threshold significantly decreased compared normal control animals. Average paw withdrawal latency in normal animals is 9.7 seconds whereas as it was 3.5 seconds in operated animals.

Ketorolac tromethamine, Composition K and Anjeso® compositions when administered intravenously at 3 mg/kg dose significantly prevented the development of mechanical allodynia at from 45 minutes onwards till 240 minutes of recording. However statistically significant effect was observed at 45, 90 and 120 minutes of recording.

Rats administered with ketorolac tromethamine (3 mg/kg; IV), Composition K (3 mg/kg; IV) and Anjeso® (3 mg/kg; IV) showed 68%, 68% and 49% increased average paw withdrawal latency respectively when compared with rats administered with vehicle (0.9% saline).

FIG. 1 discloses comparison of % change in average pain withdrawal latency in rats administered with test compounds (i.e., vehicle control (0.9% saline), ketorolac tromethamine (3 mg/kg; IV), Anjeso® (3 mg/kg; IV), Composition K (3 mg/kg; IV).

Example 8

Intravenous Pharmacokinetics Study of Meloxicam Compositions in Male Sprague-Dawley Rats Plasma pharmacokinetics of meloxicam following a single intravenous administration of two meloxicam compositions (i.e., Anjeso® and Composition K) to male Sprague-Dawley rats were investigated. The study was performed using serial sampling design (n=6 rats/group) to obtain composite pharmacokinetics profile of meloxicam in male rats.

TABLE 18

Study design

| Test item | Concentration (mg/mL) | Route/ Group No. | Gender | Dose (mg/kg) | Dose volume (mL/kg) |
|---|---|---|---|---|---|
| Anjeso ® | 30 | IV/Group 1 | Male | 10 | 0.333 |
| Composition K | 30 | IV/Group 2 | Male | 10 | 0.333 |

Blood samples (200 μL/sample) were collected from external jugular vein at pre-determined time point from each rat post injection as follows: 0.083, 0.25, 0.5, 1, 2, 4, 8 and 24 hours (Total 8 bleedings/rat) for both groups. The plasma samples were analyzed for the quantification of meloxicam in all three groups, using a fit-for purpose LC-MS/MS method with CC Range:100-50000 (ng/mL).

TABLE 19

Mean plasma pharmacokinetic parameters of meloxicam following single intravenous route of administration (ROA) of three different formulations of Meloxicam in male Sprague-Dawley rats:

| Composition administered | Group/ROA | Dose (mg/kg) | $C_{max}$ (ng/mL) | $AUC_{last}$ (h * ng/mL) | $AUC_{inf}$ (h * ng/mL) |
|---|---|---|---|---|---|
| Anjeso ® | Group 1/IV | 10 | 72772 ± 6347.9 | 555909 ± 135829 | 1001610 ± 570214 |
| Composition K | Group 2/IV | 10 | 53448 ± 2795.7 | 435866 ± 97447.0 | 634002 ± 227624 |

Example 9

Meloxicam solution having composition was set forth in Table 20.

TABLE 20

| Ingredients | Composition O (Batch size - 100 mL) | Composition P (Batch size - 100 mL) |
|---|---|---|
| Meloxicam | 30 mg | 15 mg |
| Meglumine | 20 mg | 20 mg |
| PEG-300 | 200 mg | 200 mg |
| Water for injection | q.s. to 1 mL | q.s. to 1 mL |

Manufacturing procedure of Composition O and P: About 60% quantity of the water for injection was added and heated to 50° C.-60° C. in two beakers. Specified quantities of meglumine was added to each beaker at 50° C.-60° C. and stirred continuously for 5 minutes at 500±50 RPM to obtain clear meglumine solution. Specified quantities of meloxicam was added to each beaker at 50° C.-60° C. and stirred continuously for next 60 minutes at 500±50 RPM to obtain clear meloxicam solution which was kept for cooling to room temperature under continuous stirring. Specified quantities of PEG-300 was added to each beaker and stirred continuously for next 60 minutes at 500±50 RPM to obtain clear pre-final solution. The remaining amount of water for injection was added to pre-final solution to prepare final solution.

Samples of Composition O were stored at 60° C. for 22 days, and at 40° C./75% RH for 1 month. Meloxicam solutions were clear without any particles after storing at 60° C. for 22 days.

Samples of Composition P were stored at 60° C. for 30 days, and at 40° C./75% RH for 1 month. Meloxicam solutions were clear without any particles after storing at 60° C. for 22 days and at 40° C./75% RH for 1 month.

Stability data of Composition O and P was set forth in Table 21.

TABLE 21

|  | Composition O | | | Composition P | | |
| --- | --- | --- | --- | --- | --- | --- |
| Storage Condition | Initial | 60° C. | 40° C./75% RH | Initial | 60° C. | 40° C./75% RH |
| Storage duration |  | 22 days | 1 month |  | 30 days | 1 month |
| Visual observation of solution | Clear solution |  | Tiny particles observed | Clear solution |  |  |
| pH | 8.87 | — | 8.97 | 9.73 | — | 9.73 |
| Assay | 100.9 | — | 101.3 | 99.6 | — | 98.2 |
| Osmolality | 1732 | 1730 | 1722 | 1753 | — | 1757 |
| Impurities (% w/w) | | | | | | |
| Impurity-B | 0.025 | 0.23 | 0.051 | 0.016 | — | 0.042 |
| Unspecified Impurity (at RRT) | 0.027 | 0.041 | 0.026 | 0.029 | — | 0.026 |
| Total impurities | 0.061 | 0.46 | 0.088 | 0.041 | — | 0.068 |

Example 10

Meloxicam solution having composition was set forth in Table 22.

TABLE 22

| Ingredients | Composition Q (Batch size - 100 mL/350 mL) | Composition R (Batch size - 100 mL) |
| --- | --- | --- |
| Meloxicam | 30 mg | 30 mg |
| Meglumine | 20 mg | 20 mg |
| HP-β-CD | 150 mg | 150 mg |
| Povidone K12 | 60 mg | — |
| WFI-Sterile | q.s. to 1 mL | q.s. to 1 mL |

Manufacturing procedure of Composition Q and R: About 60% quantity of water for injection was added and heated to 50° C.-60° C. in two beakers. 2 g meglumine was added to Beaker-1 & 2 at 50° C.-60° C. and stirred continuously for 5 minutes at 500±50 RPM to get clear meglumine solutions. 15 g HP-β-CD was added to Beaker-1 & 2 at 50° C.-60° C. and stirred continuously for 5 minutes at 500±50 RPM to get clear HP-β-CD solutions. 3 g meloxicam was added to Beaker-1 & 2 and were stirred continuously at temperature 50-60° C. for the next 60 minutes at 500±50 RPM to obtain clear solutions which were allowed for cooling to room temperature under continuous stirring. 6 g Povidone K12 was added to Beaker-1 and stirred continuously for 15 minutes at 500±50 RPM to get pre-final solution. The remaining amount of water for injection was added to solutions of Beaker-1 & 2 to make up to 100 mL to prepare final solution. Final solutions in Beaker-1 & 2 are Composition Q and R respectively.

Samples of Composition Q were stored at 60° C. for 18 days, and at 40° C./75% RH for 1 month. Meloxicam solutions were clear without any particles after storing at 60° C. for 18 days, and at 40° C./75% RH for 1 month.

Samples of Composition R were stored at 60° C. for 12 days, 25° C./60% RH for 1 month and at 40° C./75% RH for 1 month. Meloxicam solutions were clear without any particles after storing at 60° C. for 18 days, 25° C./60% RH for 1 month and at 40° C./75% RH for 1 month.

Stability data of Composition Q and R was set forth in Table 23.

TABLE 23

|  | Composition Q | | | | Composition R | |
| --- | --- | --- | --- | --- | --- | --- |
| Storage Condition | Initial results | 60° C. | 25° C./60% RH | 40° C./75% RH | Initial results | 60° C. |
| Storage duration |  | 1 month | 6 months | 6 months |  | 12 days |
| Visual observation of solution | Clear solution | | | | | |
| pH | 9 | 8.9 | 8.98 | 8.91 | 9.6 | NP |
| Assay | 100.6 | 99.2 | 98.6 | 98.7 | 101.4 | NP |
| Osmolality | 370 | NP | 355 | 346 | 315 | NP |
| Impurities (% w/w) | | | | | | |
| Impurity-B | 0.014 | 0.271 | 0.034 | 0.093 | ND | 0.161 |
| Unspecified Impurity (at RRT) | 0.017 (1.76) | 0.021 (0.623) | 0.013 (0.872) | 0.027 (0.079) | 0.029 (1.798) | 0.024 |
| Total impurities | 0.06 | 0.404 | 0.12 | 0.21 | 0.04 | 0.21 |

*ND = Not Detected; NP = Not Performed

Terminal sterilization data of Composition Q was set forth in Table 24.

TABLE 24

| | Composition Q | |
|---|---|---|
| Sterilization method | Autoclave at 121° C. | Autoclave at 121° C. |
| Storage duration | 15 minutes | 18 minutes |
| Visual observation of solution | Clear solution | Clear solution |
| pH | 8.99 | 8.97 |
| Assay | 102.4 | 100.5 |
| Osmolality (Osmol/Kg) | 430 | 428 |
| Impurities (% w/w) | | |
| Impurity-B | 0.264 | 0.272 |
| Oxalate Impurity | 0.009 | 0.009 |
| Unspecified Impurity (at RRT) | 0.095 (0.081) | 0.103 (0.081) |
| Total impurities | 0.475 | 0.498 |

Example 11

Meloxicam solution having composition was set forth in Table 24.

TABLE 24

| | Composition | | | | |
|---|---|---|---|---|---|
| | S | T | U | V | W |
| | Batch size | | | | |
| Ingredients | 350 mL | 350 mL | 350 mL | 350 mL | 350 mL |
| Meloxicam | 30 mg | 30 mg | 30 mg | 20 mg | 15 mg |
| Meglumine | 20 mg | 20 mg | 20 mg | 15 mg | 10 mg |
| PEG-300 | 100 mg | 80 mg | 50 mg | 100 mg | 100 mg |
| Povidone K12 | 10 mg | 10 mg | 10 mg | 10 mg | 10 mg |
| Water for injection | q.s. to 1 mL | q.s. to 1 mL | q.s. to 1 mL | q.s. to 1 mL | q.s. to 1 mL |

Manufacturing Procedures of Composition S, T, U, V and W: About 60% of water for injection was added and heated to 50° C.-60° C. in five beakers. Specified quantity of meglumine was added to beakers at 50° C.-60° C. and stirred continuously for 5 minutes at 500±50 RPM to get clear meglumine solutions. Specified quantity of meloxicam was added to beakers and were stirred continuously at temperature 50-60° C. for the next 60 minutes at 500±50 RPM to obtain clear solutions which were allowed for cooling to room temperature under continuous stirring. Specified quantity of Povidone K12 was added to beakers and stirred continuously for 15 minutes at 500±50 RPM to get povidone solutions. Specified quantity of PEG-300 was added to povidone solutions and mixed continuously for 15 minutes at 500±50 RPM to obtain clear pre-final solutions. The remaining quantity of water for injection was added to pre-final solutions to prepare final solutions.

Samples of Composition S, V and W were stored at 60° C. for 14 days (14 D), 25° C./60% RH for 1 month (1M) and at 40° C./75% RH for 1 month (1M). Meloxicam solutions were clear without any particles after storing at 60° C. for 14 days (14 D), 25° C./60% RH for 1 month (1M) and at 40° C./75% RH for 1 month (1M).

Stability data of Composition S and V was set forth in Table 25 and W was set forth in Table 26.

TABLE 25

| | Composition S | | | | Composition V | | | |
|---|---|---|---|---|---|---|---|---|
| Storage Condition | Initial | 60° C. | 25° C./ 60% RH | 40° C./ 75% RH | Initial | 60° C. | 25° C./ 60% RH | 40° C./ 75% RH |
| Storage duration | | 14D | 1M | 1M | | 14D | 1M | 1M |
| Visual observation of solution | | Clear solution | | | | Clear solution | | |
| pH | 9 | 8.99 | 8.99 | 8.97 | 9.18 | 9.15 | 9.19 | 9.19 |
| Assay | 100.1 | 103.8 | 100.8 | 100.7 | 102 | 101.5 | 102.2 | 102.1 |
| Osmolality | 661 | 670 | 658 | 657 | 626 | 631 | 619 | 620 |
| Impurities (% w/w) | | | | | | | | |
| Impurity-B | 0.012 | 0.23 | 0.025 | 0.041 | 0.012 | 0.23 | 0.025 | 0.040 |
| Unspecified Impurity (at RRT) | 0.015 (1.76) | 0.032 | 0.024 | 0.015 | 0.015 (1.76) | 0.034 | 0.016 | 0.014 |
| Total impurities | 0.06 | 0.347 | 0.104 | 0.091 | 0.05 | 0.349 | 0.068 | 0.079 |

TABLE 26

| | Composition W Storage Condition | | | |
|---|---|---|---|---|
| Storage duration | Initial | 60° C. 14 days | 25° C./ 60% RH 1M | 40° C./ 75% RH 1M |
| Visual observation of solution | Clear solution | | | |
| pH | 9.02 | 9.01 | 9.01 | 9.04 |
| Assay | 102.3 | 101.2 | 102.3 | 101.9 |
| Osmolality | 593 | 595 | 588 | 585 |
| Impurities (% w/w) | | | | |
| Impurity-B | 0.014 | 0.26 | 0.034 | 0.053 |
| Unspecified Impurity (at RRT) | 0.017 (1.76) | 0.043 | 0.016 | 0.013 |
| Total impurities | 0.06 | 0.37 | 0.085 | 0.108 |

Example 12

Meloxicam solution having composition was set forth in Table 27.

TABLE 27

| | Composition X | Composition Y | Composition Z |
|---|---|---|---|
| | | Batch size | |
| Ingredients | 500 mL | 50 mL | 50 mL |
| Meloxicam | 30 mg | 30 mg | 30 mg |
| Meglumine | 20 mg | 20 mg | 20 mg |
| PEG-400 | 100 mg | 80 mg | 50 mg |
| Povidone K12 | 10 mg | 10 mg | 10 mg |
| Water for injection | q.s. to 1 mL | q.s. to 1 mL | q.s. to 1 mL |

Manufacturing Procedures of Composition X, Y and Z: About 60% quantity of the water for injection was added and heated to 50° C.-60° C. in three beakers. Specified quantities of meglumine was added to each beaker at 50° C.-60° C. and stirred continuously for 5 minutes at 500±50 RPM to obtain clear meglumine solution. Specified quantities of meloxicam was added to each beaker at 50° C.-60° C. and stirred continuously for next 60 minutes at 500±50 RPM to obtain clear meloxicam solution which was kept for cooling to room temperature under continuous stirring. Specified quantities of Povidone K12 was added to each beaker and stirred continuously for next 15 minutes at 500±50 RPM to obtain clear povidone solution. Specified quantities of PEG-400 was added to each beaker and stirred continuously for next 5 minutes at 500±50 RPM to obtain clear pre-final solution. The remaining amount of water for injection was added to pre-final solution to prepare final solution.

Stability data of Composition X, Y and Z was set forth in Table 28.

TABLE 28

| | Composition X Storage Condition | | |
|---|---|---|---|
| Storage duration | Initial | 25° C./ 60% RH 1 month | 40° C./ 75% RH 1 month |
| Visual observation of solution | Clear solution | | |
| pH | 8.97 | 8.97 | 8.97 |
| Assay | 100.2 | 98.0 | 98.1 |

TABLE 28-continued

| | Composition X Storage Condition | | |
|---|---|---|---|
| Storage duration | Initial | 25° C./ 60% RH 1 month | 40° C./ 75% RH 1 month |
| Osmolality | 567 | 560 | 568 |
| Impurities (% w/w) | | | |
| Impurity-B | 0.01 | 0.026 | 0.057 |
| Unspecified Impurity (at RRT) | 0.016 | 0.015 | 0.013 |
| Total impurities | 0.028 | 0.073 | 0.116 |

Example 13

Meloxicam solution having composition was set forth in Table 29.

TABLE 29

| | Composition ZA | Composition ZB | Composition ZC |
|---|---|---|---|
| | | Batch size | |
| Ingredients | 50 mL | 350 mL | 350 mL |
| Meloxicam | 30 mg | 30 mg | 30 mg |
| Meglumine | 20 mg | 20 mg | 20 mg |
| PEG-300 | 100 mg | 80 mg | 50 mg |
| Povidone K12 | 10 mg | 10 mg | 10 mg |
| Hydrochloric acid (1N) | pH adjusted to 8.0 | — | — |
| Water for injection | q.s. to 1 mL | q.s. to 1 mL | q.s. to 1 mL |

Manufacturing Procedure of Compositions ZA, ZB and ZC: About 60% quantity of water for injection was heated to 50° C.-60° C. in a suitable container. Specified amount of meglumine was added to the purified water at 50° C.-60° C. and stirred continuously for 5 minutes at 500±50 RPM or until a clear solution is obtained to get meglumine solution. Specified quantity of meloxicam was added to the meglumine solution and mixed continuously at temperature 50-60° C. for next 60 minutes at 500±50 RPM or until a clear solution was obtained to get meloxicam solution which was allowed for cooling to room temperature under continuous stirring. Specified quantity of Povidone K12 was added to the meloxicam solution and mixed continuously for 15 minutes at 500±50 RPM or until a clear solution was obtained to get povidone solution. Specified quantity of PEG-400 was added to povidone solution and mixed continuously for 5 minutes at 500±50 RPM or until a clear solution is obtained to get pre-final solution. The remaining amount of water for injection was added to the pre-final solution to prepare final solution. For the Composition ZA, the pH of the final solution was adjusted to 8 with 1N hydrochloric acid.

Example 14

Intravenous Pharmacokinetics Study of Meloxicam Compositions in Male Sprague-Dawley Rats Plasma pharmacokinetics of meloxicam following a single intravenous administration of two meloxicam compositions (i.e., Anjeso® and Composition Q) to male Sprague-Dawley rats were investigated. The study was performed using serial sampling design (n=8 rats/group) to obtain composite pharmacokinetics profile of meloxicam in male rats.

TABLE 31

Study design

| Test item | Concentration (mg/mL) | Route/ Group No. | Gender | Dose (mg/kg) | Dose volume (mL/kg) |
|---|---|---|---|---|---|
| Anjeso ® | 30 | IV/Group 1 | Male | 10 | 0.333 |
| Composition Q | 30 | IV/Group 2 | Male | 10 | 0.333 |

Blood samples (200 μL/sample) were collected from external jugular vein at pre-determined time point from each rat post injection as follows: 0.033, 0.083, 0.25, 0.5, 1, 2, 4, 8, 24, 48, 72 and 96 hours (Total 12 bleedings/rat) for both groups. The plasma samples were analyzed for the quantification of meloxicam in both groups, using a fit-for purpose LC-MS/MS method with CC Range:100-50000 (ng/mL).

TABLE 32

Mean plasma pharmacokinetic parameters of meloxicam following single intravenous route of admininstration (ROA) of two different formulations of Meloxicam in male Sprague-Dawley rats.

| Composition administered | Group/ ROA | Dose (mg/kg) | $C_0$ (ng/mL) | $AUC_{last}$ (h * ng/mL) | $AUCi_{nf}$ (h * ng/mL) |
|---|---|---|---|---|---|
| Composition Q (Test) | Group 1/IV | 10 | 106000 | 1730000 | 1930000 |
| Anjeso ® (Reference) | Group 2/IV | 10 | 97900 | 1420000 | 1740000 |

In conclusion, the Composition Q had showed comparable pharmacokinetics profile with that of ANJESO® following a single intravenous route of administration in Male Sprague-Dawley rats. Test/Reference ratio was found to be 1.08, 1.22 and 1.11 for $C_0$ (ng/mL), $AUC_{last\ (h.ng/mL)}$ and $AUC_{inf}$ (h.ng/mL) respectively.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:

1. An injectable solution suitable for parenteral administration comprising:
    (a) about 30 mg/mL of meloxicam,
    (b) one or more pharmaceutically acceptable solvents; and
    (c) a solubilizer, wherein the solubilizer comprises a combination of meglumine and a cyclodextrin derivative,
        wherein the concentration of meglumine is between 10 mg/mL and 50 mg/mL;
        wherein the concentration of the cyclodextrin derivative is from about 5 mg/mL to about 250 mg/mL;
        wherein the solution is a ready-to-use formulation, and
        wherein the solution is stable and remains clear when stored for 6 months at 40° C./75% RH, and.

2. The solution according to claim 1, wherein the solution has a pH in the range of about 7 to about 10.

3. The solution according to claim 1, wherein the solution has an osmolality between about 100 mOsm and about 2000 mOsm.

4. The solution according to claim 1, wherein the meloxicam and the meglumine are used at a molar ratio of 0.5:1 to 0.5:10.

5. The solution according to claim 1, wherein the meloxicam and the meglumine are used at a molar ratio of 1:0.5 to 10:1.

6. The solution according to claim 1, wherein the concentration of the meglumine is between 15 mg/mL and 30 mg/mL.

7. The solution according to claim 1, wherein the concentration of the meglumine is 20 mg/mL.

8. The solution according to claim 1, wherein the cyclodextrin derivative is hydroxypropyl-β-cyclodextrin (HP-β-CD), and wherein the meloxicam and the HP-β-CD are used in a molar ratio of 0.5:1 to 0.5:10.

9. The solution according to claim 1, wherein the concentration of the cyclodextrin derivative is from about 5 mg/mL to about 220 mg/mL.

10. The solution according to claim 1, comprising
    about 20 mg/mL of the meglumine,
    about 150 mg/mL of the cyclodextrin derivative.

11. The solution according to claim 1, further comprising 60 mg/mL of povidone.

12. The solution according to claim 1, wherein the pharmaceutically acceptable solvent is water.

13. The solution according to claim 1, wherein the cyclodextrin derivative is hydroxypropyl-β-cyclodextrin (HP-β-CD).

14. The solution according to claim 1, wherein the solution is prepared by:
    (i) adding the meglumine with stirring to water, at a temperature of about 50° C. to about 60° C. to form a first solution;
    (ii) adding the cyclodextrin derivative with stirring to the first solution, at a temperature of about 50° C. to about 60° C. to form a second solution;
    (iii) adding the meloxicam with stirring to the second solution, at a temperature of about 50° C. to about 60° C. to form the solution according to claim 1.

* * * * *

UNITED STATES PATENT AND TRADEMARK OFFICE
CERTIFICATE OF CORRECTION

PATENT NO. : 12,263,176 B2
APPLICATION NO. : 18/542163
DATED : April 1, 2025
INVENTOR(S) : Ashish Anilrao Dubewar et al.

It is certified that error appears in the above-identified patent and that said Letters Patent is hereby corrected as shown below:

In the Claims

In Claim 1, at Column 48, Line 10:
"stored for 6 months at 40° C./75% RH, and." should read --stored for 6 months at 40° C./75% RH.--.

Signed and Sealed this
Eighth Day of July, 2025

Coke Morgan Stewart
*Acting Director of the United States Patent and Trademark Office*